US011090253B2

(12) United States Patent
Bouzeloc et al.

(10) Patent No.: US 11,090,253 B2
(45) Date of Patent: *Aug. 17, 2021

(54) COSMETIC COMPOSITION COMPRISING SILICONE MATERIALS

(71) Applicant: Dow Silicones Corporation, Midland, MI (US)

(72) Inventors: Sylvie Bouzeloc, Seneffe (BE); Tatiana Dimitrova, Seneffe (BE); Charlene Fournier, Seneffe (BE); Frederic Gubbels, Seneffe (BE)

(73) Assignee: DOW SILICONES CORPORATION, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/322,923

(22) PCT Filed: Aug. 3, 2017

(86) PCT No.: PCT/EP2017/069748
§ 371 (c)(1),
(2) Date: Feb. 1, 2019

(87) PCT Pub. No.: WO2018/024860
PCT Pub. Date: Feb. 8, 2018

(65) Prior Publication Data
US 2020/0214967 A1    Jul. 9, 2020

(30) Foreign Application Priority Data
Aug. 3, 2016 (GB) .................................... 1613397

(51) Int. Cl.
*A61K 8/89* (2006.01)
*A61K 8/04* (2006.01)
*A61K 8/06* (2006.01)
*A61Q 5/02* (2006.01)
*A61Q 5/12* (2006.01)

(52) U.S. Cl.
CPC ............... *A61K 8/89* (2013.01); *A61K 8/042* (2013.01); *A61K 8/046* (2013.01); *A61K 8/064* (2013.01); *A61Q 5/02* (2013.01); *A61Q 5/12* (2013.01)

(58) Field of Classification Search
None
See application file for complete search history.

(56) References Cited

U.S. PATENT DOCUMENTS

| 3,030,371 | A | 4/1962 | Walter |
| 3,334,067 | A | 8/1967 | Weyenberg |
| 3,419,516 | A | 12/1968 | Tarno |
| 4,087,585 | A | 5/1978 | Schulz |
| 4,754,013 | A | 6/1988 | Antonen |
| 4,908,140 | A | 3/1990 | Bausch et al. |
| 5,089,253 | A | 2/1992 | Halloran |
| 5,126,389 | A | 6/1992 | Ona et al. |
| 5,194,649 | A | 3/1993 | Okawa |
| 5,232,611 | A | 8/1993 | Ohashi et al. |
| 5,262,088 | A | 11/1993 | Hill et al. |
| 5,281,455 | A | 1/1994 | Braun et al. |
| 5,300,171 | A | 4/1994 | Braun et al. |
| 5,380,464 | A | 1/1995 | McGee et al. |
| 5,684,110 | A | 11/1997 | Kawamura |
| 5,804,631 | A | 9/1998 | Mine et al. |
| 5,840,794 | A | 11/1998 | Palmer |
| 6,015,784 | A | 1/2000 | Kazuta et al. |
| 6,169,142 | B1 | 1/2001 | Nakano et al. |
| 6,521,587 | B1 | 2/2003 | L'Hostis et al. |
| 6,534,581 | B1 | 3/2003 | Kleyer et al. |
| 6,593,413 | B2 | 7/2003 | Muramatsu et al. |
| 6,642,309 | B2 | 11/2003 | Komitsu et al. |
| 7,144,953 | B2 | 12/2006 | Ueda et al. |
| 7,417,105 | B2 | 8/2008 | Landon et al. |
| 7,893,170 | B2 | 2/2011 | Wakioka et al. |
| 7,951,458 | B2 | 5/2011 | Ogura et al. |
| 7,973,108 | B2 | 7/2011 | Okamoto et al. |
| 8,030,371 | B2 | 10/2011 | Chaussade |
| 8,231,944 | B1 | 7/2012 | Schroeder |
| 8,536,109 | B2 | 9/2013 | Delbrassinne et al. |
| 8,609,797 | B2 | 12/2013 | Knepper et al. |
| 8,686,094 | B2 | 4/2014 | Djurdjevic et al. |
| 8,785,537 | B2 | 7/2014 | Carrard et al. |

(Continued)

FOREIGN PATENT DOCUMENTS

| CN | 1365379 A | 8/2002 |
| CN | 105440693 A | 3/2016 |
| CN | 105505297 A | 4/2016 |
| EP | 217501 A2 | 4/1987 |
| EP | 341952 A2 | 11/1989 |
| EP | 356210 A2 | 2/1990 |
| EP | 393511 A2 | 10/1990 |
| EP | 0393511 A2 | 10/1990 |
| EP | 539234 A2 | 4/1993 |
| EP | 2221328 A2 | 8/2010 |
| EP | 2221329 A2 | 8/2010 |
| EP | 2792690 A1 | 10/2014 |
| FR | 2910301 A1 | 6/2008 |

(Continued)

OTHER PUBLICATIONS

Romerskincare ([retrieved from on-line website: https://www.romerskincare.com/ingredient-glossary/, last visit Nov. 5, 2020]) (Year: 2020).*

(Continued)

*Primary Examiner* — Kyung S Chang
(74) *Attorney, Agent, or Firm* — Warner Norcross + Judd LLP

(57) ABSTRACT

Cosmetic compositions comprising silicone based materials cured via a condensation cure chemistry are disclosed. In particular, the present disclosure relates to cosmetic compositions comprising a silicone based gel cured via a condensation cure chemistry; and at least one cosmetic ingredient, optionally in a cosmetically acceptable medium. Preparation methods and uses of the cosmetic compositions are also disclosed.

14 Claims, No Drawings

(56) References Cited

U.S. PATENT DOCUMENTS

| | | |
|---|---|---|
| 8,801,890 B2 | 8/2014 | Verosky et al. |
| 9,051,435 B2 | 6/2015 | Takei et al. |
| 9,228,061 B2 | 1/2016 | Brandstadt et al. |
| 9,493,689 B2 | 11/2016 | Stanjek et al. |
| 9,527,985 B2 | 12/2016 | Okamatsu |
| 9,732,203 B2 | 8/2017 | Okamatsu |
| 10,150,888 B2 | 12/2018 | Simon et al. |
| 10,414,907 B2 | 9/2019 | Takahara |
| 10,563,015 B2 | 2/2020 | Gubbels et al. |
| 2002/0010251 A1 | 1/2002 | Muramatsu et al. |
| 2002/0193273 A1 | 12/2002 | Richards, III et al. |
| 2003/0119917 A1 | 6/2003 | Fey et al. |
| 2004/0002571 A1 | 1/2004 | Sakamoto et al. |
| 2006/0122295 A1 | 6/2006 | Oysaed et al. |
| 2006/0194067 A1 | 8/2006 | Beger et al. |
| 2006/0258818 A1 | 11/2006 | Kimura et al. |
| 2007/0173597 A1 | 7/2007 | Williams et al. |
| 2007/0219299 A1 | 9/2007 | Okamoto et al. |
| 2007/0237912 A1 | 10/2007 | Correia |
| 2007/0244249 A1 | 10/2007 | Correia |
| 2007/0282047 A1 | 12/2007 | Kimura et al. |
| 2007/0287780 A1 | 12/2007 | Wakabayashi et al. |
| 2008/0033087 A1 | 2/2008 | Okamoto et al. |
| 2008/0076878 A1 | 3/2008 | Wakioka et al. |
| 2008/0172807 A1 | 7/2008 | Brun |
| 2008/0179616 A1 | 7/2008 | Lee et al. |
| 2008/0194773 A1 | 8/2008 | Wakioka et al. |
| 2008/0279901 A1 | 11/2008 | Prigent et al. |
| 2008/0284106 A1 | 11/2008 | Maton et al. |
| 2008/0287636 A1 | 11/2008 | Wakabayashi et al. |
| 2008/0292572 A1 | 11/2008 | Benabdillah |
| 2008/0312365 A1 | 12/2008 | Maton et al. |
| 2008/0312366 A1 | 12/2008 | Maton et al. |
| 2008/0312367 A1 | 12/2008 | Maton et al. |
| 2008/0319152 A1 | 12/2008 | Okamoto et al. |
| 2009/0029043 A1 | 1/2009 | Rong et al. |
| 2009/0215944 A1 | 8/2009 | Maton et al. |
| 2009/0234052 A1 | 9/2009 | Maton et al. |
| 2010/0093598 A1 | 4/2010 | Davio et al. |
| 2010/0137454 A1 | 6/2010 | Barmes et al. |
| 2010/0144585 A1 | 6/2010 | Aksoy et al. |
| 2010/0184883 A1 | 7/2010 | Detemmerman et al. |
| 2011/0003081 A1 | 1/2011 | Maton et al. |
| 2011/0028646 A1 | 2/2011 | Sixt et al. |
| 2011/0144246 A1 | 6/2011 | Dabbous et al. |
| 2011/0165206 A1 | 7/2011 | Liu et al. |
| 2011/0248314 A1 | 10/2011 | Takei et al. |
| 2012/0016063 A1 | 1/2012 | Maton et al. |
| 2012/0022209 A1 | 1/2012 | Djurdjevic et al. |
| 2012/0022210 A1 | 1/2012 | Davio et al. |
| 2012/0123537 A1 | 5/2012 | Manesis et al. |
| 2012/0214902 A1 | 8/2012 | Detemmerman et al. |
| 2012/0214925 A1 | 8/2012 | Gubbels et al. |
| 2013/0338289 A1 | 12/2013 | Jadot et al. |
| 2014/0024731 A1 | 1/2014 | Blanc et al. |
| 2014/0235812 A1 | 8/2014 | Brandstadt et al. |
| 2014/0238471 A1 | 8/2014 | Wakita et al. |
| 2014/0256539 A1 | 9/2014 | Takei et al. |
| 2014/0350176 A1 | 11/2014 | Fisher et al. |
| 2014/0364515 A1 | 12/2014 | Zeng et al. |
| 2015/0007938 A1 | 1/2015 | Stanjek et al. |
| 2015/0166859 A1 | 6/2015 | Choffat et al. |
| 2015/0183951 A1 | 7/2015 | Bhagwagar et al. |
| 2015/0224036 A1* | 8/2015 | Hasegawa ............ A61Q 17/04 424/401 |
| 2015/0257988 A1 | 9/2015 | Hasegawa |
| 2015/0315437 A1 | 11/2015 | Albaugh et al. |
| 2016/0009883 A1 | 1/2016 | Pernot |
| 2017/0002201 A1 | 1/2017 | Von Malotki et al. |
| 2018/0009951 A1 | 1/2018 | Gubbels et al. |
| 2018/0237720 A1 | 8/2018 | Barnes et al. |
| 2019/0177486 A1 | 6/2019 | Baily et al. |
| 2019/0177584 A1 | 6/2019 | Gubbels et al. |
| 2019/0291024 A1 | 9/2019 | Rahma et al. |
| 2019/0338077 A1 | 11/2019 | Chambard et al. |
| 2020/0140617 A1 | 5/2020 | Gubbels et al. |
| 2020/0190324 A1 | 6/2020 | Gubbels |
| 2020/0392431 A1 | 12/2020 | Ugazio et al. |
| 2020/0398537 A1 | 12/2020 | Gubbels et al. |
| 2020/0399514 A1 | 12/2020 | Gubbels et al. |

FOREIGN PATENT DOCUMENTS

| | | |
|---|---|---|
| GB | 2424898 A | 10/2006 |
| JP | S5269460 A | 6/1977 |
| JP | H08269331 A | 10/1996 |
| JP | H08302193 A | 11/1996 |
| JP | 2000178448 A | 6/2000 |
| JP | 2000281523 A | 10/2000 |
| JP | 2001200161 A | 7/2001 |
| JP | 2002205911 A | 7/2002 |
| JP | 2002235004 A | 8/2002 |
| JP | 2003226812 A | 8/2003 |
| JP | 2004035631 A | 2/2004 |
| JP | 2006342327 A | 12/2006 |
| JP | 2007119695 A | 5/2007 |
| JP | 2008163021 A | 7/2008 |
| JP | 2008174554 A | 7/2008 |
| JP | 2008179616 A | 8/2008 |
| JP | 2010248446 A | 11/2010 |
| JP | 2011137119 A | 7/2011 |
| JP | 2012251058 A | 12/2012 |
| JP | 5180140 B2 | 4/2013 |
| JP | 2013234245 A | 11/2013 |
| JP | 5621211 B2 | 11/2014 |
| JP | 2016128497 A | 7/2016 |
| WO | 2001042365 A1 | 6/2001 |
| WO | 2001096463 A2 | 12/2001 |
| WO | 2007117551 A1 | 10/2007 |
| WO | 2007117552 A1 | 10/2007 |
| WO | 2008045395 A1 | 4/2008 |
| WO | 2008045417 A2 | 4/2008 |
| WO | 2008045427 A1 | 4/2008 |
| WO | 2009013309 A1 | 1/2009 |
| WO | 2009128883 A1 | 10/2009 |
| WO | 2010115782 A2 | 10/2010 |
| WO | 2010117744 A2 | 10/2010 |
| WO | 2010143357 A1 | 12/2010 |
| WO | 2013036548 A2 | 3/2013 |
| WO | 2013100175 A1 | 7/2013 |
| WO | 2014022377 A1 | 2/2014 |
| WO | 2016120270 A1 | 8/2016 |
| WO | 2017030128 A1 | 2/2017 |
| WO | 2017191322 A1 | 11/2017 |
| WO | 2018024856 A1 | 2/2018 |
| WO | 2018024857 A1 | 2/2018 |
| WO | 2018024858 A1 | 2/2018 |
| WO | 2018024859 A1 | 2/2018 |
| WO | 2018024860 A1 | 2/2018 |
| WO | 2018024865 A1 | 2/2018 |
| WO | 2018050503 A1 | 3/2018 |
| WO | 2018200796 A1 | 11/2018 |

OTHER PUBLICATIONS

Machine assisted English translation of JP2016128497A obtained from https://patents.google.com/patent on Apr. 3, 2020, 17 pages.
Machine assisted English translation of JP2000178448A obtained from https://patents.google.com/patent on Jul. 8, 2020, 10 pages.
Machine assisted English translation of JP2000281523A obtained from https://patents.google.com/patent on Jul. 8, 2020, 23 pages.
Machine assisted English translation of JP2002205911A obtained from https://patents.google.com/patent on Jul. 8, 2020, 12 pages.
Machine assisted English translation of JP2002235004A obtained from https://patents.google.com/patent on Jul. 8, 2020, 11 pages.
Machine assisted English translation of JP2003226812A obtained from https://patents.google.com/patent on Jul. 8, 2020, 17 pages.
Machine assisted English translation of JP2008174554A obtained from https://patents.google.com/patent on Jul. 8, 2020, 21 pages.
International Search Report for related Application No. PCT/EP2017/069748 dated Sep. 9, 2017, 4 pages.

(56) References Cited

OTHER PUBLICATIONS

Lee, et al, 1970 Journal of Polymer Science Part A-2, Polymer Physics.
Michael A. Brook, Silicon in Organic, Organometallic and Polymer Chemistry, John Wiley & sons, Inc. (2000), pp. 285-287.
Mills, E., European Polymer Journal, 1969, vol. 5, pp. 675-695.
Noll, W.; Chemistry and Technology of Silicones, Academic Press Inc., New York, 1968, pp. 397-399.
O'Lenick, Jr., Basic Silicone Chemistry—A Review, Aug. 1999, Silicone Spectator, Jan. 2009.
International Search Report for Application No. PCT/EP2016/051573, dated Mar. 11, 2016, 4 pages.
International Search Report for Application No. PCT/EP2017/069743, dated Nov. 14, 2017, 3 pages.
International Search Report for Application No. PCT/EP2017/069744, dated Nov. 9, 2017, 3 pages.
International Search Report for Application No. PCT/EP2017/069745, dated Nov. 9, 2017, 3 pages.
International Search Report for Application No. PCT/EP2017/069746, dated Oct. 30, 2017, 4 pages.
International Search Report for Application No. PCT/EP2017/069749, dated Oct. 30, 2017, 4 pages.
International Search Report for Application No. PCT/EP2017/069753, dated Nov. 14, 2017, 3 pages.
Machine assisted English translation of CN105440693A obtained from https://patents.google.com/patent on Mar. 8, 2021, 6 pages.
Machine assisted English translation of CN105505297A obtained from https://patents.google.com/patent on Mar. 8, 2021, 10 pages.
Machine assisted English translation of CN1365379A obtained from https://patents.google.com/patent on Mar. 8, 2021, 12 pages.
Machine assisted English translation of JP2001200161A obtained from https://patents.google.com/patent on Mar. 8, 2021, 7 pages.
Machine assisted English translation of JP2006342327A obtained from https://patents.google.com/patent on Mar. 8, 2021, 9 pages.
Machine assisted English translation of JP2007119695A obtained from https://patents.google.com/patent on Mar. 8, 2021, 9 pages.
Machine assisted English translation of JP2010248446A obtained from https://patents.google.com/patent on Mar. 8, 2021, 10 pages.
Machine assisted English translation of JP2011137119A obtained from https://patents.google.com/patent on Mar. 8, 2021, 13 pages.
Machine assisted English translation of JP2012251058A obtained from https://patents.google.com/patent on Mar. 8, 2021, 16 pages.
Machine assisted English translation of JP2013234245A obtained from https://patents.google.com/patent on Mar. 8, 2021, 8 pages.
Machine assisted English translation of JP5180140B2 obtained from https://patents.google.com/patent on Mar. 8, 2021, 10 pages.
Machine assisted English translation of JP5621211B2 obtained from https://patents.google.com/patent on Mar. 8, 2021, 10 pages.
Machine assisted English translation of JPH08269331A obtained from https://patents.google.com/patent on Mar. 8, 2021, 8 pages.
Machine assisted English translation of JPH08302193A obtained from https://patents.google.com/patent on Mar. 8, 2021, 7 pages.
Machine assisted English translation of JPS5269460A obtained from https://worldwide.espacenet.com/patent on Mar. 8, 2021, 10 pages.
Machine assisted English translation of WO2010143357A1 obtained from https://patents.google.com/patent on Mar. 8, 2021, 13 pages.
Machine assisted English translation of WO2017030128A1 obtained from https://patents.google.com/patent on Mar. 8, 2021, 18 pages.

* cited by examiner

COSMETIC COMPOSITION COMPRISING SILICONE MATERIALS

CROSS-REFERENCE TO RELATED APPLICATIONS

This application is the National Stage of International Application No. PCT/EP2017/069748 filed on 3 Aug. 2017, where the invention claims priority from patent application GB1613397.7 filed on Aug. 3, 2016 and from patent application GB1701915.9 filed on Mar. 6, 2017.

FIELD OF THE INVENTION

This disclosure relates to cosmetic compositions comprising a silicone based material cured via a condensation cure chemistry (M), and at least one cosmetic ingredient, in a cosmetically acceptable medium. Also disclosed is a process to prepare the cosmetic compositions and their uses to care for keratinous substrates.

BACKGROUND OF THE INVENTION

Silicone materials of various kinds may be prepared using various reaction systems. Examples of silicone materials include at least straight-chain polymers, branched polymers, elastomeric polymers, gums, resinous structures. These silicone materials vary in their polymeric structure, in their viscosity or consistency, and in a lot of general properties such as hardness, flowability, stickiness, compatibility.

A variety of reaction mechanisms exist to produce the wide variety of silicone materials. Examples include hydrosilylation cure or addition cure, making use of vinyl-functional polymers, oligomers with Si—H groups, and a metal complex catalyst, such as platinum (Pt); peroxide cure or free radical cure utilizing free radicals generated by organic peroxides that decompose at elevated temperatures, initiating a crosslinking reaction; and condensation cure.

Silicone materials find uses in cosmetic applications for sensory benefits, conditioning benefits or in some instance, as rheology modifiers.

There is an ongoing need for silicone materials which provide for care of keratinous substrates and improved aesthetics in cosmetic applications. There is for example a continuing need for hair care compositions that give hair shiny appearance without an oily feel and look. In addition, there is a need for composition with good in-use experience, that look and feel better, and are more stable over time in terms of phase separation and aggregation. There is further a need for cosmetic compositions which provide improved coverage and hiding of wrinkles, fine lines, and pores, with improved moisturizing effect, while also providing a smooth, light feeling to the skin.

DETAILED DESCRIPTION

The present invention relates to cosmetic compositions comprising silicone based material cured via a condensation cure chemistry. In particular, the present disclosure relates to cosmetic compositions comprising a silicone based material cured via a condensation cure chemistry; and at least one cosmetic ingredient, in a cosmetically acceptable medium; where the silicone based material cured via a condensation cure chemistry is the condensation reaction product of:
(i) at least one condensation curable silyl terminated polymer having at least one, typically at least 2 hydrolysable and/or hydroxyl functional groups per molecule;
(ii) a cross-linker selected from silanes having at least 2 hydrolysable groups and/or silyl functional molecules having at least 2 silyl groups, each silyl group containing at least one hydrolysable group; and
(iii) a condensation catalyst selected from the group of titanates or zirconates characterized in that the molar ratio of hydroxyl groups to hydrolysable groups is between 0.4:1 to 2:1 using a monosilane cross linker or 0.2:1 to 10:1 using disilyl crosslinker and the molar ratio of M-OR functions to the hydroxyl groups is comprised between 0.01:1 and 0.6:1, where M is titanium or zirconium.

The condensation cured silicone material typically exhibits a hardness below Shore 80 in the type 00 scale according to ASTM D 2240-05(2010). Products having a hardness of Shore below 0 in the 00 scale, i.e. soft materials may also be obtained. The hardness of such materials are typically measured with the help of a penetrometer. The condensation cured materials can also be in a liquid (flowable) form, that is, in a form where the material can be poured from one container into another under the sole influence of gravity within minutes (in less than 60 minutes). In some instances the material may also be a thick paste that is not typically pourable, but "pumpable", that is, it may be transferred from one recipient to the other by a pumping device.

The present silicone based materials cured via a condensation cure chemistry may have different viscosity/consistency ranging from a flowable polymers with various elasticity to gels of different hardness. These materials may be used in cosmetic applications, where they provide for conditioning benefits when present in a shampoo; hold when present in a leave in conditioner; smooth skin feel when present in a skin care cream; SPF boost when present in a sun care cream.

The terms "silanol", "hydroxysilyl", "hydroxyl", "SiOH" may be used interchangeably in the scope of the present invention, to indicate a condensation curable silyl terminating group of a polymer, bearing at least one hydroxyl functional group.

The terms "alkoxy", "hydrolysable", "SiOR" may be used interchangeably in the scope of the present invention, to indicate a condensation curable silyl terminating group of a polymer, bearing at least one hydrolysable functional group.

The terms "ratio SiOH/SiOR", "ratio hydroxyl groups to hydrolysable groups", "ratio silanol/alkoxy groups" may also be used interchangeably, in the scope of the present invention.

The relationship of molecular weight to viscosity of polydimethylsiloxane is described in scientific literature, for example, in at least Mills, E., European Polymer Journal, 1969, vol. 5, p. 675-695. The formula published in this article can be used to calculate approximately the weight average molecular weight of polymers (Mw) with an accuracy of about 10%. For condensation polymerization, the polydispersity index (PI) is the ratio Mw/Mn, and is approximately 2. From this relationship, the average molecular weight in number (Mn) can be calculated.

The Mn and Mw of silicone can also be determined by Gel Permeation Chromatography (GPC) with a precision of about 10-15%. This technique is a standard technique, and yields values for Mw (weight average), Mn (number average) and polydispersity index (PI) (where PI=Mw/Mn).

Mn value provided in this application have been determined by GPC and represent a typical value of the polymer used. If not provided by GPC, the Mn may also be obtained from calculation based on the dynamic viscosity of said polymer.

For example, the silanol content in mmol per 100 g of the Hydroxydimethylsilyl terminated polydimethyl siloxane can be determined with the average molecular weight in number (Mn) of the polymer using the following formula:

SiOH content (mmol/100 g of polymer)=2×100×1000/Mn (where 100 is for amount in grams, 1000 is for mmol)

Similarly, the SiOR content in mmol per 100 g of the Trialkoxysilyl terminated polydimethylsiloxane of 56,000 mPa·s can be determined with the average molecular weight in number (Mn) of the polymer using the following formula: SiOR content (mmol/100 g of polymer)=F×100×1000/Mn where F represents the number of alkoxy function (SiOR) present in the polymer, i.e., 6 for hexa alkoxy functional polymers (and where 100 is for amount in grams, 1000 is for mmol).

For non-polymeric molecules the following formula can be used SiOR content (mmol/100 g of polymer)=F×100×1000/MW where F represents the number of alkoxy function present in the molecule and MW is the molecular weight of the molecule (and where 100 is for amount in grams, 1000 is for mmol).

The silanol molar content related to a polymer is equal to the amount in g of hydroxyl terminated polymer in 100 g of the mixed product divided by the average molecular weight in number of the polymer multiply by the average number of hydroxyl functions present in the polymer, typically 2. If there are several hydroxyl functional polymers in the formulation, the sum of the molar content of each polymer is summed up to constitute the total silanol molar content in the formulation. The total silanol molar content is calculated for 100 g of the mixed formulation.

The alkoxy molar content related to a substance is equal to the amount in g of alkoxy functional molecule in 100 g of the mixed product divided by the molecular weight of the molecule or the average molecular weight in number in case it is polymeric alkoxy functional molecule multiply by the average number of alkoxy functions present in the molecule. The sum of the molar content of each molecule or polymer is summed up to constitute the total alkoxy molar content in the formulation. The total alkoxy molar content is calculated for 100 g of the mixed formulation.

The silanol to alkoxy molar ratio is then calculated by dividing the total silanol molar content by the total alkoxy molar content.

Polymer (i) is at least one or alternatively a moisture/condensation curable silyl terminated polymer. Any suitable moisture/condensation curable silyl terminated polymer may be utilised including polydialkyl siloxanes, alkylphenyl siloxane, or organic based polymers with silyl terminal groups e.g. silyl polyethers, silyl acrylates and silyl terminated polyisobutylenes or copolymers of any of the above. Polymer (i) may be selected from polysiloxane based polymer containing at least two hydroxyl or hydrolysable groups and/or organic based polymer having silyl terminal groups, each bearing at least one hydrolysable group.

The polymer (i) may be a polysiloxane based polymer containing at least two hydroxyl or hydrolysable groups, alternatively, the polymer comprises terminal hydroxyl or hydrolysable groups.

Examples of suitable hydroxyl or hydrolysable groups include —Si(OH)$_3$, —(R$^a$)Si(OH)$_2$, —(R$^a$)$_2$Si(OH), —R$^a$Si(OR$^b$)$_2$, —Si(OR$^b$)$_3$, —R$^a{}_2$SiOR$^b$ or —(R$^a$)$_2$ Si—R$^c$—SiR$^d{}_k$(OR$^b$)$_{3-k}$ where each R$^a$ independently represents a monovalent hydrocarbyl group, for example, an alkyl group, in particular having from 1 to 8 carbon atoms; each R$^b$ and R$^d$ group is independently an alkyl or alkoxy group in which the alkyl groups suitably have up to 6 carbon atoms; R$^c$ is a divalent hydrocarbon group which may be interrupted by one or more siloxane spacers having up to six silicon atoms; and k has the value 0, 1 or 2.

Polymer (i) may have the general formula (1)

X$^3$-A-X$^1$ (1)

where X$^3$ and X$^1$ are independently selected from siloxane groups which terminate in hydroxyl or hydrolysable groups and A is a siloxane containing polymeric chain.

Examples of hydroxyl-terminating or hydrolysable groups X$^3$ or X$^1$ include —Si(OH)$_3$, —(R$^a$)Si(OH)$_2$, —(R$^a$)$_2$Si(OH), —(R$^a$)Si(OR$^b$)$_2$, —Si(OR$^b$)$_3$, —(R$^a$)$_2$Si-OR$^b$ or —(R$^a$)$_2$ Si—R$^c$—Si(R$^d$)$_p$(OR$^b$)$_{3-p}$ as defined above with each R$^b$ group, when present, typically being a methyl group. The X$^3$ and/or X$^1$ terminal groups may be hydroxydialkyl silyl groups, e.g. hydroxydimethyl silyl groups or alkoxydialkyl silyl groups e.g. methoxydimethyl silyl or ethoxydimethyl silyl.

Examples of suitable siloxane groups in polymeric chain A of formula (1) are those which comprise a polydiorganosiloxane chain. Thus polymeric chain A may include siloxane units of formula (2)

—(R$^5{}_s$SiO$_{(4-s)/2}$)— (2)

in which each R$^5$ is independently an organic group such as a hydrocarbyl group having from 1 to 10 carbon atoms optionally substituted with one or more halogen group such as chlorine or fluorine and s is 0, 1 or 2. Particular examples of groups R$^5$ include methyl, ethyl, propyl, butyl, vinyl, cyclohexyl, phenyl, tolyl group, a propyl group substituted with chlorine or fluorine such as 3,3,3-trifluoropropyl, chlorophenyl, beta-(perfluorobutyl)ethyl or chlorocyclohexyl group. Suitably, at least some or substantially all of the groups R$^5$ are methyl.

It is conceivable to provide a molecule/polymer having phenyl/aryl groups among the functional groups, directly bonded to the silicon atom, e.g. R$^5$=phenyl in the formula above, or bonded to the silicon atom via a hydrocarbon bridging group, e.g. R$^5$=CxH2x-phenyl in the formula above. Such aryl functional polymer may contain of from 10 to 50 mol % of aryl group. The refractive index of such a molecule/polymer may be ranging of from 1.41 to 1.56. Such molecule/polymer may find uses in skin care and hair care applications, providing for either shine on lips from lip care products, or for shine on hair from leave on or rinse off products.

For the purpose of this application "substituted" means one or more hydrogen atoms in a hydrocarbon group has been replaced with another substituent. Examples of such substituents include, but are not limited to, halogen atoms such as chlorine, fluorine, bromine, and iodine; halogen atom containing groups such as chloromethyl, perfluorobutyl, trifluoroethyl, and nonafluorohexyl; oxygen atoms; oxygen atom containing groups such as (meth)acrylic and carboxyl; nitrogen atoms; nitrogen atom containing groups such as amino-functional groups, amido-functional groups, and cyano-functional groups; sulphur atoms; and sulphur atom containing groups such as mercapto groups.

Typically the polymers of the above type will have a viscosity in the order of 1,000 to 300,000 mPa·s, alternatively 1,000 to 100,000 mPa·s at 25° C. measured by using a Brookfield cone plate viscometer (RV DIII) using a cone plate.

Typical polymer (i) containing units of formula (2) are thus polydiorganosiloxanes having terminal, silicon-bound hydroxyl groups or terminal, silicon-bound organic radicals which can be hydrolysed using moisture as defined above. The polydiorganosiloxanes may be homopolymers or copolymers. Mixtures of different polydiorganosiloxanes having terminal condensable groups are also suitable.

The polymer (i) may alternatively be an organic based polymer having silyl terminal groups, each bearing at least one hydrolysable group. Typical silyl terminal groups include silyl polyethers, silyl acrylates and silyl terminated polyisobutylenes.

In the case of silyl polyethers, the polymer chain is based on polyoxyalkylene based units (organic). Such polyoxyalkylene units preferably comprise a linear predominantly oxyalkylene polymer comprised of recurring oxyalkylene units, ($—C_nH_{2n}—O—$) illustrated by the average formula ($—C_nH_{2n}—O—)_m$ wherein n is an integer from 2 to 4 inclusive and m is an integer of at least four. The average molecular weight of each polyoxyalkylene polymer block may range from about 300 to about 10,000, but can be higher in molecular weight. Moreover, the oxyalkylene units are not necessarily identical throughout the polyoxyalkylene monomer, but can differ from unit to unit. A polyoxyalkylene block, for example, can be comprised of oxyethylene units, ($—C_2H_4—O—$); oxypropylene units ($—C_3H_6—O—$); or oxybutylene units, ($—C_4H_8—O—$); or mixtures thereof.

Other polyoxyalkylene units may include for example: units of the structure

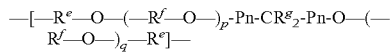

in which Pn is a 1,4-phenylene group, each $R^e$ is the same or different and is a divalent hydrocarbon group having 2 to 8 carbon atoms, each $R^f$ is the same or different and is an ethylene group or propylene group, each $R^g$ is the same or different and is a hydrogen atom or methyl group and each of the subscripts p and q is a positive integer in the range from 3 to 30.

The backbone of the organic section of polymer (i) which may contain organic leaving groups within the molecule, is not particularly limited and may be any of organic polymers having various backbones. The backbone may include at least one selected from a hydrogen atom, a carbon atom, a nitrogen atom, an oxygen atom, and a sulphur atom because the resulting composition has excellent curability.

Crosslinkers (ii) that can be used are generally moisture curing
  silanes having at least 2 hydrolysable groups, alternatively at least 3 hydrolysable groups per molecule group; and/or
  silyl functional molecules having at least 2 silyl groups, each silyl group containing at least one hydrolysable group.

Typically, a cross-linker requires a minimum of 2 hydrolysable groups per molecule and preferably 3 or more. In some instances, the crosslinker (ii) having two hydrolysable groups may be considered a chain extender. The crosslinker (ii) may thus have two but alternatively has three or four silicon-bonded condensable (preferably hydroxyl and/or hydrolysable) groups per molecule which are reactive with the condensable groups in organopolysiloxane polymer (i).

For the sake of the disclosure herein a monosilane cross-linker shall be understood to mean a molecule containing a single silyl functional group, which contains at least two hydrolysable groups.

For the sake of the disclosure herein a disilyl functional molecule is a silyl functional molecule containing two silyl groups, each silyl group containing at least one hydrolysable group. The disilyl functional molecule comprises two silicon atoms having each at least one hydrolysable group, where the silicon atoms are separated by an organic or siloxane spacer. Typically, the silyl groups on the disilyl functional molecule may be terminal groups. The spacer may be a polymeric chain.

For the sake of the disclosure herein a disilane is a silyl functional molecule having at least 2 silyl groups where the two silicon atoms are bonded to one another.

The hydrolysable groups on the silyl groups include acyloxy groups (for example, acetoxy, octanoyloxy, and benzoyloxy groups); ketoximino groups (for example dimethyl ketoximo, and isobutylketoximino); alkoxy groups (for example methoxy, ethoxy, and propoxy) and alkenyloxy groups (for example isopropenyloxy and 1-ethyl-2-methylvinyloxy). In some instances, the hydrolysable group may include hydroxyl groups.

The monosilane cross-linker (ii) include alkoxy functional silanes, oximosilanes, acetoxy silanes, acetonoxime silanes, enoxy silanes.

When the crosslinker is a silane and when the silane has three silicon-bonded hydrolysable groups per molecule, the fourth group is suitably a non-hydrolysable silicon-bonded organic group. These silicon-bonded organic groups are suitably hydrocarbyl groups which are optionally substituted by halogen such as fluorine and chlorine. Examples of such fourth groups include alkyl groups (for example methyl, ethyl, propyl, and butyl); cycloalkyl groups (for example cyclopentyl and cyclohexyl); alkenyl groups (for example vinyl and allyl); aryl groups (for example phenyl, and tolyl); aralkyl groups (for example 2-phenylethyl) and groups obtained by replacing all or part of the hydrogen in the preceding organic groups with halogen. The fourth silicon-bonded organic groups may be methyl.

A typical monosilane may be described by formula (3)

wherein $R^5$ is described above and r has a value of 2, 3 or 4. Typical silanes are those wherein R" represents methyl, ethyl or vinyl or isobutyl. R" is an organic radical selected from linear and branched alkyls, allyls, phenyl and substituted phenyls, acethoxy, oxime. In some instances, $R^5$ represents methyl or ethyl and r is 3.

Another type of suitable crosslinkers (ii) are molecules of the type $Si(OR^5)_4$ where $R^5$ is as described above, alternatively propyl, ethyl or methyl. Partials condensates of $Si(OR^5)_4$ may also be considered.

In one embodiment the cross-linker (ii) is a silyl functional molecule having at least 2 silyl groups having each at least 1 and up to 3 hydrolysable groups, alternatively each silyl group has at least 2 hydrolysable groups.

The crosslinker (ii) may be a disilyl functional polymer, that is, a polymer containing two silyl groups, each containing at least one hydrolysable group such as described by the formula (4)

where y and z are independently an integer of 1, 2 or 3, alternatively 2 or 3. Rv is an organic or polysiloxane-based fragment.

The disilyl functional crosslinker (ii) may have a siloxane or organic polymeric backbone. In the case of such siloxane or organic based cross-linkers the molecular structure can be straight chained, branched, cyclic or macromolecular. Suitable polymeric crosslinkers (ii) may have a similar polymeric backbone chemical structure to polymeric chain A as depicted in formula (1) above.

Examples of disilyl polymeric crosslinkers (ii) with a silicone or organic polymer chain bearing alkoxy functional end groups include 1,6-bis(trimethoxysilyl)hexane (alternatively known as hexamethoxydisilylhexane HMSH), polydimethylsiloxanes having at least one trialkoxy terminal where the alkoxy group may be a methoxy or ethoxy group.

Further examples of disilyl polymeric crosslinkers (ii) may be described by the general formula (5)

$$W-B-W$$

where W is $-Si(R^8)_2\text{-}(D)_f\text{-}R^9-Si\ R^8{}_t(OR^{12})_{3-t}$ and
D is $-R^9-(Si(R^8)_2-O)_h-Si\ (R^8)_2-$
$R^8$ represents an alkyl group having from 1 to 6 carbon atoms, a vinyl group or a phenyl group, or fluorinated alkyl
$R^9$ is a divalent hydrocarbon group
h is an integer between 1 and 6
f is 0 or an integer,
$R^{12}$ is an alkyl or alkoxy group in which the alkyl groups have up to 6 carbon atoms and
t has the value 0, 1 or 2
and where B represents a substantially linear backbone, which can be either organic or polysiloxane based, optionally having maximum of 5% branching.

A typical organic backbone B will be a polyether. A typical siloxane-based backbone B will be $-[SiO_{(4-j)/2}(R^1)_j]_w-$ where w is an integer from 50 to 5000; j is on average from 1.9 to 2; $R_1$ is selected from monovalent alkyl radical form 1 to 10 carbon atoms (alternatively 1 to 4 carbon atoms) or from monovalent halohydrocarbon radicals, cyanoalkyl radicals all with less than 18 carbon atoms.

In some instances, $R^8$ is methyl, $R^9$ is either a methylene or ethylene group, t is 0 or 1, $R^{12}$ is a methyl or ethyl group. In some instances, at least one W group is a $-Si(R^8)_2\text{-}(D)_f\text{-}R^9-SiR^8{}_t(O\ R^{12})_{3-t}$ group. A small proportion of W groups may be Si(alkyl)$_3$- groups (where the alkyl groups are preferably methyl groups).

Crosslinkers (ii) thus include alkyltrialkoxysilanes such as methyltrimethoxysilane (MTM) and methyltriethoxysilane, tetraethoxysilane, partially condensed tetraethoxysilane, alkenyltrialkoxy silanes such as vinyltrimethoxysilane and vinyltriethoxysilane, isobutyltrimethoxysilane (iBTM). Other suitable silanes include ethyltrimethoxysilane, vinyltriethoxysilane, phenyltrimethoxysilane, alkoxytrioximosilane, alkenyltrioximosilane, 3,3,3-trifluoropropyltrimethoxysilane, methyltriacetoxysilane, vinyltriacetoxysilane, ethyl triacetoxysilane, di-butoxy diacetoxysilane, phenyl-tripropionoxysilane, methyltris(methylethylketoximo)silane, vinyl-tris-methylethylketoximo)silane, methyltris(methylethylketoximino)silane, methyltris(isopropenoxy)silane, vinyltris(isopropenoxy)silane, ethylpolysilicate, n-propylorthosilicate, ethylorthosilicate, dimethyltetraacetoxydisiloxane, oximosilanes, acetoxy silanes, acetonoxime silanes, enoxy silanes and other such trifunctional alkoxysilanes as well as partial hydrolytic condensation products thereof; bis(trialkoxysilylalkyl)amines, bis(dialkoxyalkylsilylalkyl)amine, bis[trialkoxysilylalkyl)N-alkylamine, bis[dialkoxyalkylsilylalkyl)N-alkylamine, bis(trialkoxysilylalkyl)urea, bis(dialkoxyalkylsilylalkyl) urea, bis [3-trimethoxysilylpropyl)amine, bis[3-triethoxysilylpropyl) amine, bis[4-trimethoxysilylbutyl)amine, bis[4-triethoxysilylbutyl)amine, bis[3-trimethoxysilylpropyl)N-methylamine, bis[3-triethoxysilylpropyl)N-methylamine, bis[4-trimethoxysilylbutyl)N-methylamine, bis[4-triethoxysilylbutyl)N-methylamine, bis[3-trimethoxysilylpropyl) urea, bis[3-triethoxysilylpropyl)urea, bis[4-trimethoxysilylbutyl)urea, bis[4-triethoxysilylbutyl)urea, bis[3-dimethoxymethylsilylpropyl)amine, bis[3-diethoxymethyl silylpropyl)amine, bis[4-dimethoxymethylsilylbutyl)amine, bis[4-diethoxymethyl silylbutyl)amine, bis[3-dimethoxymethylsilylpropyl)N-methylamine, bis[3-diethoxymethylsilylpropyl)N-methylamine, bis[4-dimethoxymethylsilylbutyl)N-methylamine, bis[4-diethoxymethyl silylbutyl)N-methylamine, bis[3-dimethoxymethylsilylpropyl)urea, bis [3-diethoxymethyl silylpropyl)urea, bis[4-dimethoxymethylsilylbutyl)urea, bis[4-diethoxymethyl silylbutyl)urea, bis[3-dimethoxyethylsilylpropyl)amine, bis [3-diethoxyethyl silylpropyl)amine, bis[4-dimethoxyethylsilylbutyl)amine, bis[4-diethoxyethyl silylbutyl)amine, bis [3-dimethoxyethylsilylpropyl)N-methylamine, bis[3-diethoxyethyl silylpropyl)N-methylamine, bis[4-dimethoxyethylsilylbutyl)N-methylamine, bis[4-diethoxyethyl silylbutyl)N-methylamine, bis[3-dimethoxyethylsilylpropyl)urea bis[3-diethoxyethyl silylpropyl)urea, bis[4-dimethoxyethylsilylbutyl)urea and/or bis[4-diethoxyethyl silylbutyl)urea; bis(triethoxysilylpropyl)amine, bis(trimethoxysilylpropyl)amine, bis[trimethoxysilylpropyl)urea, bis[triethoxysilylpropyl)urea, bis (diethoxymethylsilylpropyl)N-methylamine; Di or Trialkoxy silyl terminated polydialkyl siloxane, di or trialkoxy silyl terminated polyarylalkyl siloxanes, di or trialkoxy silyl terminated polypropyleneoxide, polyurethane, polyacrylates; polyisobutylenes; Di or triacetoxy silyl terminated polydialkyl; polyarylalkyl siloxane; Di or trioximino silyl terminated polydialkyl; polyarylalkyl siloxane; Di or triacetonoxy terminated polydialkyl or polyarylalkyl. The cross-linker (ii) used may also comprise any combination of two or more of the above.

The molar ratio of hydroxyl groups to hydrolysable groups is between 0.4:1 to 2:1 using a monosilane cross-linker or 0.2:1 to 10:1, alternatively 0.1:1 to 10:1, alternatively 0.1:1 to 3:1, using a disilyl functional cross-linker.

The composition further comprises a condensation catalyst. This increases the speed at which the composition cures. The catalyst chosen for inclusion in a particular silicone composition depends upon the speed of cure required.

Titanate and/or zirconate based catalysts may comprise a compound according to the general formula Ti[OR$^{22}$]$_4$ or Zr[OR$^{22}$]$_4$ where each R$^{22}$ may be the same or different and represents a monovalent, primary, secondary or tertiary aliphatic hydrocarbon group which may be linear or branched containing from 1 to 10 carbon atoms. Optionally the titanate and/or zirconate may contain partially unsaturated groups. Examples of R$^{22}$ include but are not restricted to methyl, ethyl, propyl, isopropyl, butyl, tertiary butyl and a branched secondary alkyl group such as 2, 4-dimethyl-3-pentyl. Alternatively, when each R$^{22}$ is the same, R$^{22}$ is an isopropyl, branched secondary alkyl group or a tertiary alkyl group, in particular, tertiary butyl. Suitable titanate examples include tetra n-butyl titanate, tetra t-butyl titanate, titanium tetrabutoxide and tetraisopropyl titanate. Suitable zirconate examples include tetra-n-propyl zirconate, tetra-n-butyl zirconate and zirconium diethylcitrate.

Alternatively, the titanate and/or zirconate may be chelated. The chelation may be with any suitable chelating agent such as an alkyl acetylacetonate such as methyl or ethylacetylacetonate. Alternatively, the titanate may be monoalkoxy titanates bearing three chelating agents such as for example 2-propanolato, tris isooctadecanoato titanate or diisopropyldiethylacetoacetate titanate. Further chelates include aminoalcohol ester chelates such as triethanolamine titanate chelate, diethanolamine titanate or di-isopropoxybis-(beta-diethanolamine ethoxy) titanate. Further chelates include organic acid or salt chelates such as the ammonium salt of a lactic acid titanate chelate.

The molar ratio of M-OR functions to the hydroxyl groups is comprised between 0.01:1 and 0.6:1, where M is titanium or zirconium. When a low amount of catalyst is used, it might be beneficial to premix the catalyst with the crosslinker or with an optional diluent, thus allowing for a more reliable dosing. This process is typical for a person skilled in the art, and is sometimes referred to as "masterbatch".

In some instances, the composition used to cure the material is a mixture of a condensation curable polymer (i), cross-linker (ii) and condensation catalyst (iii) as described above in combination with a hydrosilylation curable polymer together with a suitable cross-linker and hydrosilylation catalyst. Any suitable polymer curable via a hydrosilylation reaction pathway may be utilized. Such hydrosilylation curable polymers are known in the art. In some instances, the composition used to cure the material is a mixture of a condensation curable polymer (i), cross-linker (ii) and condensation catalyst (iii) as described above free of hydrosilylation curable polymer, hydrosilylation cross-linker and hydrosilylation catalyst.

The material as hereinbefore described is typically made from the condensation curable material composition which is stored in a 2 part manner, that is, in parts I and II. The two part compositions may be mixed using any appropriate standard two-part mixing equipment with a dynamic or static mixer.

Typically, the condensation curable composition is stored in two parts having polymer (i) and cross-linker (ii) in part I and polymer (i) and catalyst (iii) in part II. In some instances, the condensation curable composition is stored in two parts having cross-linker (ii) in part I and polymer (i) and catalyst (iii) in part II. In some further instances, the condensation curable composition is stored in two parts having a first polymer (i) and cross-linker (ii) in part I and a second polymer (ii) and catalyst (iii) in part II. The catalyst is typically held separate from polymers (i) and (ii) until condensation reaction is desired to start. When additives are present, these may be present in any of parts I and II or in both parts.

The condensation curable material composition based on titanate/zirconate cure catalysts can be cured to a bulk cure in a few minutes to a few weeks, alternatively in a few minutes to a few hours, depending on the composition. Typically, the curing reaction takes place at temperatures ranging of from 15 to 80° C., alternatively 20 to 50° C., alternatively 20-25° C.

In neat form, the cured silicone based material may be in the form of a thick polymer, a gel, a branched polymer, an elastomeric structured siloxane. Neat form in the scope if the present invention means the material is comprised of the reaction product of the reactant polymer (i), crosslinker (ii) and catalyst (iii). Viscosities and consistencies of the neat material may vary. Characterization methods includes the use of a texture analyser, to assess hardness or penetration. Materials typically having a penetration positive force at 5 mm of maximum 10 g are easier to handle and are easier to emulsify. The material characterization may be carried out after reaction is fully complete, after several hours. In some instances, material characterization may be carried out after more than 7 days.

The present silicone based material cured via a condensation cure chemistry may be prepared in presence of a diluent. In such instances, the cured silicone based material may be in diluted form.

Examples of diluents include silicon containing diluents such as hexamethyldisiloxane, octamethyltrisiloxane, and other short chain linear siloxanes such as octamethyltrisiloxane, decamethyltetrasiloxane, dodecamethylpentasiloxane, tetradecamethylhexasiloxane, hexadeamethylheptasiloxane, heptamethyl-3-{(trimethylsilyl)oxy)}trisiloxane, cyclic siloxanes such as hexamethylcyclotrisiloxane, octamethylcyclotetrasiloxane, decamethylcyclopentasiloxane, dodecamethylcyclohexasiloxane; further polydiorganosiloxanes, optionally including aryl functional siloxanes, having a viscosity of from 500 to 12,500 mPa·s, measured at 25° C.; organic diluents such as butyl acetate, alkanes, alcohols, ketones, esters, ethers, glycols, glycol ethers, hydrocarbons, hydrofluorocarbons or any other material which can dilute the composition without adversely affecting any of the component materials. The diluent might be a mixture of two or more diluents. Hydrocarbons include isododecane, isohexadecane, Isopar L (C11-C 13), Isopar H (C11-C12), hydrogenated polydecene, mineral oil, especially hydrogenated mineral oil or white oil, liquid polyisobutene, isoparaffinic oil or petroleum jelly. Ethers and esters include isodecyl neopentanoate, neopentylglycol heptanoate, glycol distearate, dicaprylyl carbonate, diethylhexyl carbonate, propylene glycol n butyl ether, ethyl-3 ethoxypropionate, propylene glycol methyl ether acetate, tridecyl neopentanoate, propylene glycol methylether acetate (PGMEA), propylene glycol methylether (PGME), octyldodecyl neopentanoate, diisobutyl adipate, diisopropyl adipate, propylene glycol dicaprylate/dicaprate, and octyl palmitate. Additional organic diluents include fats, oils, fatty acids, and fatty alcohols. A mixture of diluents may also be used.

The weight ratio of cured silicone material to diluent can for example be 100/0 to 10/90, alternatively 70/30 to 20/80. The diluent may be added before, after or during the condensation reaction of the silicone based material occurs, although it does not contribute to or participate in the condensation reaction. For ease of handling, the diluent may be added before the condensation reaction is initiated. The diluent may be present in any or both of parts I and II.

The present silicone based material cured via a condensation cure chemistry may be provided in emulsion form, which may be prepared by any known methods, or alternatively prepared by the methods as discussed below.

The present disclosure further provides a process for preparing an emulsion by:
I) forming a mixture comprising;
  A) 100 parts by weight of silicone based material cured via a condensation cure chemistry,
  B) 0.1 to 50 parts by weight of a surfactant,
II) admixing a sufficient amount of water to the mixture from step I) to form an emulsion,
III) optionally, further shear mixing the emulsion and/or diluting of the emulsion with the continuous phase.

The amount of surfactant added in step I should be 0.1 to 50 parts by weight, alternatively 1 to 50 parts by weight, alternatively 2 to 20 parts by weight, for every 100 parts by weight of silicone based material.

Mixing in step (I) can be accomplished by any method known in the art to effect mixing of high viscosity materials. The mixing may occur either as a batch, semi-continuous, or continuous process. Mixing may occur, for example using, batch mixing equipment with medium/low shear include change-can mixers, double-planetary mixers, conical-screw mixers, ribbon blenders, double-arm or sigma-blade mixers; batch equipment with high-shear and high-speed dispersers include those made by Charles Ross & Sons (NY), Hockmeyer Equipment Corp. (NJ); batch equipment with high shear actions include Banbury-type (CW Brabender Instruments Inc., NJ) and Henschel type (Henschel mixers America, TX); centrifugal force-based, high shear mixing devices as for example Speed Mixer® (Hauschild & Co KG, Germany). Illustrative examples of continuous mixers/compounders include extruders single-screw, twin-screw, and multi-screw extruders, co-rotating extruders, such as those manufactured by Krupp Werner & Pfleiderer Corp (Ramsey, N.J.), and Leistritz (NJ); twin-screw counter-rotating extruders, two-stage extruders, twin-rotor continuous mixers, dynamic or static mixers or combinations of this equipment.

The temperature and pressure at which the mixing of step I occurs is not critical, but generally is conducted at ambient temperature (20-25° C.) and pressures. Typically, the temperature of the mixture will increase during the mixing process due to the mechanical energy associated when shearing such high viscosity materials.

Step II of the process involves admixing water to the mixture of step I to form an emulsion. Typically 5 to 2000 parts by weight water are mixed for every 100 parts by weight of the step I mixture to form an emulsion. The water is added to the mixture from step I at such a rate, with additional mixing, so as to form an emulsion of the mixture of step I. While this amount of water can vary depending on the selection of the surfactants, generally the amount of water is from 0.1 to 2000 parts per 100 parts by weight of the step I mixture, alternatively from 5 to 500 parts per 100 parts by weight of the step I mixture, or alternatively from 5 to 100 parts per 100 parts by weight of the step I mixture.

The addition of water to the mixture from step I may be done in incremental portions, whereby each incremental portion comprises less than 30 weight % of the mixture from step I and each incremental portion of water is added successively to the previous after the dispersion of the previous incremental portion of water, wherein sufficient incremental portions of water are added to form an emulsion of the silicone based material.

Mixing in step (II) can be accomplished by any method known in the art to effect mixing of high viscosity materials. The mixing may occur either as a batch, semi-continuous, or continuous process. Any of the mixing methods as described for step (I), may be used to effect mixing in step (II). Alternatively, mixing in step (II) may also occur via those techniques known in the art to provide high shear mixing to effect formation of emulsions. Representative of such high shear mixing techniques include: homogenizers, sonolators, and other similar shear devices.

Optionally, the emulsion formed in step (II) may be further sheared according to step (III) to reduce particle size and/or improve long term storage stability. The shearing may occur by any of the mixing techniques discussed above. In some cases it might be necessary to run one or several of the steps I to III under lower pressure or vacuum.

The present disclosure further provides a first alternative process for preparing an emulsion by;
I) forming a mixture comprising;
  A) 100 parts by weight of
    (i) at least one condensation curable silyl terminated polymer having at least one, typically at least 2 hydrolysable and/or hydroxyl functional groups per molecule;
    (ii) a cross-linker selected from silanes having at least 2 hydrolysable groups and/or silyl functional molecules having at least 2 silyl groups, each silyl group containing at least one hydrolysable group; and
    (iii) a condensation catalyst selected from the group of titanates or zirconates characterized in that the molar ratio of hydroxyl groups to hydrolysable groups is between 0.4:1 to 2:1 using a monosilane cross linker or 0.2:1 to 10:1 using disilyl crosslinker and the molar ratio of M-OR functions to the hydroxyl groups is comprised between 0.01:1 and 0.6:1, where M is titanium or zirconium;
    (iv) an optional diluent;
  B) 0.1 to 50 parts by weight of a surfactant,
II) admixing a sufficient amount of water to the mixture from step I) to form an emulsion,
III) optionally, further shear mixing the emulsion and/or diluting of the emulsion with the continuous phase,
IV) subsequently allowing the condensation cure reaction to take place after the emulsification is complete.

In this alternative process, the mixing and addition conditions remain as disclosed for the first process. The reaction conditions are also as discussed above.

The surfactant may be an anionic surfactant, cationic surfactant, nonionic surfactant, amphoteric surfactant, or a mixture of any of these surfactants.

Examples of anionic surfactants include alkali metal, amine, or ammonium salts of higher fatty acids, alkylaryl sulphonates such as sodium dodecyl benzene sulfonate, long chain fatty alcohol sulfates, olefin sulfates and olefin sulfonates, sulfated monoglycerides, sulfated esters, sulfonated ethoxylated alcohols, sulfosuccinates, alkane sulfonates, phosphate esters, alkyl isethionates, alkyl taurates, alkyl sarcosinates, and mixtures thereof.

Examples of cationic surfactants include alkylamine salts, quaternary ammonium salts, sulphonium salts, and phosphonium salts. Examples of suitable nonionic surfactants include condensates of ethylene oxide with long chain fatty alcohols or fatty acids such as a C12-16 alcohol, condensates of ethylene oxide with an amine or an amide, condensation products of ethylene and propylene oxide, esters of glycerol, sucrose, sorbitol, fatty acid alkylol amides, sucrose esters, fluoro-surfactants, fatty amine oxides, and mixtures thereof.

Examples of amphoteric surfactants include imidazoline compounds, alkylaminoacid salts, betaines, and mixtures thereof.

Examples of nonionic surfactants include polyoxyethylene fatty alcohols such as polyoxyethylene (23) lauryl ether, polyoxyethylene (4) lauryl ether; ethoxylated alcohols such as ethoxylated trimethylnonanol, C12-C14 secondary alcohol ethoxylates, ethoxylated, C10-Guerbet alcohol, ethoxylated, iso-C13 alcohol; poly(oxyethylene)-poly(oxypropylene)-poly(oxyethylene) tri-block copolymer (also referred to as poloxamers); tetrafunctional poly(oxyethylene)-poly(oxypropylene) block copolymer derived from the sequential addition of propylene oxide and ethylene oxide to ethylene diamine (also referred to as poloxamines), silicone polyethers, and mixtures thereof.

The emulsions of the present disclosure may be an oil/water emulsion, a water/oil emulsion, a multiple phase or triple emulsion.

In one embodiment, the emulsions of the present disclosure are oil/water emulsions. The present oil/water emulsions may be characterized by average volume particle of the dispersed (oil) phase in the continuous aqueous phase. The particle size may be determined by laser diffraction of the emulsion. Suitable laser diffraction techniques are well known in the art. The particle size is obtained from a particle size distribution (PSD). The PSD can be determined on a volume, surface, length basis. The volume particle size is equal to the diameter of the sphere that has the same volume as a given particle. The term Dv represents the average volume particle size of the dispersed particles. Dv 0.5 is the particle size measured in volume corresponding to 50% of the cumulative particle population. In other words if Dv 0.5=10 μm, 50% of the particle have an average volume particle size below 10 μm and 50% of the particle have a volume average particle size above 10 μm. Unless indicated otherwise all average volume particle sizes are calculated using Dv 0.5.

The average volume particle size of the dispersed siloxane particles in the oil/water emulsions may vary between 0.1 μm and 150 μm; or between 0.1 μm and 30 μm; or between 0.2 μm and 5.0 μm.

The present disclosure provides a second alternative process for preparing an emulsion by:

A) forming a semi-cured mixture comprising:
  (i) 100 parts by weight of at least one condensation curable silyl terminated polymer having at least one, typically at least 2 hydrolysable and/or hydroxyl functional groups per molecule;
  (ii) a cross-linker selected from silanes having at least 2 hydrolysable groups and/or silyl functional molecules having at least 2 silyl groups, each silyl group containing at least one hydrolysable group; and
  (iii) a condensation catalyst selected from the group of titanates or zirconates characterized in that the molar ratio of hydroxyl groups to hydrolysable groups is between 0.4:1 to 2:1 using a monosilane cross linker or 0.2:1 to 10:1 using disilyl crosslinker and the molar ratio of M-OR functions to the hydroxyl groups is comprised between 0.01:1 and 0.6:1, where M is titanium or zirconium;
  (iv) an optional diluent;
  (v) mixing the parts (i) to (iv) and letting cure to proceed until the penetration force F(+) as measured at 5 mm penetration by TA.XT Plus Texture Analyser (available from Texture Technologies and equipped with rounded-end plastic probe) is above 1.2 g but below 4 g. Alternatively a two-fold increase in viscosity with regard to catalyst—free mix measured at 20 RPM, 20-23 C at 30% relative humidity using a cone-plate Brookfield viscometer.
B) 0.1 to 50 parts by weight of a surfactant,
C) admixing a sufficient amount of water to the mixture from step A) to form an emulsion,
D) optionally, further shear mixing the emulsion and/or diluting of the emulsion with the continuous phase,
E) subsequently allowing the condensation cure reaction to complete upon the end of the emulsification process.

In this second alternative process, the mixing and addition conditions remain as disclosed for the first alternative process. The reaction conditions are also as discussed above.

The surfactant may be an anionic surfactant, cationic surfactant, nonionic surfactant, amphoteric surfactant, or a mixture of any of these surfactants. Examples of each of these surfactants are provided above.

The silicone material cured via a condensation cure chemistry is present in a cosmetic composition in conjunction with a cosmetic ingredient, optionally in a cosmetically acceptable medium.

Cosmetic compositions include those compositions which are intended to be placed in contact with the external parts of the human body (skin (epidermis), hair system, nails, mucosa, etc., also referred to as "keratinous substrates") or with the teeth and the mucous membranes of the oral cavity with a view exclusively or mainly to cleaning them, perfuming them, changing their appearance, protecting them, keeping them in good condition or correcting body odours. In some instances, cosmetic compositions may also include health care compositions. The present cosmetic compositions do not include (that is, exclude) patches for skin care delivery of actives, be it in health care or in skin care.

Cosmetic ingredients are those ingredients known to be used in cosmetic application. A wide review of such ingredients may be found in the CTFA cosmetic ingredient handbook. Cosmetically acceptable medium include water, solvents, diluents, or mixtures and emulsions thereof.

Cosmetic ingredients include emollients, waxes, moisturizers, surface active materials such as surfactants or detergents or emulsifiers, thickeners, water phase stabilizing agents, pH controlling agents, preservatives and cosmetic biocides, sebum absorbants or sebum control agents, vegetable or botanical extracts, vitamins, proteins or amino-acids and their derivatives, pigments, colorants, fillers, silicone conditioning agents, cationic conditioning agents, hydrophobic conditioning agents, UV absorbers, sunscreen agents, antidandruff agents, antiperspirant agents, deodorant agents, skin protectants, hair dyes, nail care ingredients, fragrances or perfume, antioxidants, oxidizing agents, reducing agents, propellant gases, film formers and mixtures thereof. The cosmetic ingredient may be different from a filler.

Additional ingredients that may be used in the cosmetic compositions include fatty alcohols, colour care additives, anticellulites, pearlising agents, chelating agents, styling agents, ceramides, suspending agents and others.

Health care ingredients include antiacne agents, antibacterial agents, antifungal agents, therapeutic active agents, external analgesics, skin bleaching agents, anti-cancer agents, diuretics, agents for treating gastric and duodenal ulcers, proteolytic enzymes, antihistamine or H1 histamine blockers, sedatives, bronchodilators, diluents.

Additional ingredients that may be used in the health care compositions include antibiotic, antiseptic, antibacterial, anti-inflammatory, astringents, hormones, smoking cessation compositions, cardiovascular, antiarrythmic, alpha-I blocker, beta blocker, ACE inhibitor, antiaggregant, non-steroidal anti-inflammatory agents such as diclofenac, antipsoriasis agents such as clobetasol propionate, antidermatitis agents, tranquillizer, anticonvulsant, anticoagulant agents, healing factors, cell growth nutrients, peptides, corticosteroidal drugs, antipruritic agents and others.

Cosmetic ingredients may be used in health care compositions, such as waxes, and others; and health care ingredients may be used in cosmetic compositions such as anti-acne agents, and others.

Examples of emollients include volatile or non-volatile silicone oils; silicone resins such as polypropylsilsesquioxane and phenyl trimethicone; silicone elastomers such as dimethicone crosspolymer; alkylmethylsiloxanes such as C30-45 Alkyl Methicone; volatile or non-volatile hydrocarbon compounds, such as squalene, paraffin oils, petrolatum oils and naphthalene oils; hydrogenated or partially hydrogenated polyisobutene; isoeicosane; squalane; isoparaffin; isododecane; isodecane or isohexa-decane; branched C8-C16 esters; isohexyl neopentanoate; ester oils such as isononyl isononanoate, cetostearyl octanoate, isopropyl myristate, palmitate derivatives, stearates derivatives, isostearyl isostearate and the heptanoates, octanoates, decanoates or ricinoleates of alcohols or of polyalcohols, or mixtures thereof; hydrocarbon oils of plant origin, such as wheatgerm, sunflower, grapeseed, castor, shea, avocado, olive, soybean, sweet almond, palm, rapeseed, cotton seed, hazelnut, macadamia, jojoba, blackcurrant, evening primrose; or triglycerides of caprylic/capric acids; higher fatty acids, such as oleic acid, linoleic acid or linolenic acid, and mixtures thereof.

Example of waxes include hydrocarbon waxes such as beeswax, lanolin wax, rice wax, carnauba wax, candelilla wax, microcrystalline waxes, paraffins, ozokerite, polyethylene waxes, synthetic wax, ceresin, lanolin, lanolin derivatives, cocoa butter, shellac wax, bran wax, capok wax, sugar cane wax, montan wax, whale wax, bayberry wax, silicone waxes (e.g. polymethylsiloxane alkyls, alkoxys and/or esters, C30-45 alkyldimethylsilyl polypropylsilsesquioxane), and mixtures thereof.

Examples of moisturizers include lower molecular weight aliphatic diols such as propylene glycol and butylene glycol; polyols such as glycerine and sorbitol; and polyoxyethylene polymers such as polyethylene glycol 200; hyaluronic acid and its derivatives, and mixtures thereof.

Examples of surface active materials may be anionic, cationic or non-ionic, and include organomodified silicones such as dimethicone copolyol; oxyethylenated and/or oxypropylenated ethers of glycerol; oxyethylenated and/or oxypropylenated ethers of fatty alcohols such as ceteareth-30, C12-15 pareth-7; fatty acid esters of polyethylene glycol such as PEG-50 stearate, PEG-40 monostearate; saccharide esters and ethers, such as sucrose stearate, sucrose cocoate and sorbitan stearate, and mixtures thereof; phosphoric esters and salts thereof, such as DEA oleth-10 phosphate; sulphosuccinates such as disodium PEG-5 citrate lauryl sulphosuccinate and disodium ricinoleamido MEA sulphosuccinate; alkyl ether sulphates, such as sodium lauryl ether sulphate; isethionates; betaine derivatives; and mixtures thereof. The surface active materials may be the same or different from the surfactants used for emulsification, as discussed above.

Further examples of nonionic surfactants include polyoxyethylene alkyl ethers, polyoxyethylene alkylphenol ethers, polyoxyethylene lauryl ethers, polyoxyethylene sorbitan monoleates, polyoxyethylene alkyl esters, polyoxyethylene sorbitan alkyl esters, polyethylene glycol, polypropylene glycol, diethylene glycol, ethoxylated trimethylnonanols, polyoxyalkylene-substituted silicones (rake or ABn types), silicone alkanolamides, silicone esters, silicone glycosides, and mixtures thereof.

Nonionic surfactants include dimethicone copolyols, fatty acid esters of polyols, for instance sorbitol or glyceryl mono-, di-, tri- or sesquioleates or stearates, glyceryl or polyethylene glycol laurates; fatty acid esters of polyethylene glycol (polyethylene glycol monostearate or monolaurate); polyoxyethylenated fatty acid esters (stearate or oleate) of sorbitol; polyoxyethylenated alkyl (lauryl, cetyl, stearyl or octyl)ethers.

Anionic surfactants include carboxylates (sodium 2-(2-hydroxyalkyloxy)acetate)), amino acid derivatives (N-acylglutamates, N-acylgly-cinates or acylsarcosinates), alkyl sulfates, alkyl ether sulfates and oxyethylenated derivatives thereof, sulfonates, isethionates and N-acylisethionates, taurates and N-acyl N-methyltaurates, sulfosuccinates, alkylsulfoacetates, phosphates and alkyl phosphates, polypeptides, anionic derivatives of alkyl polyglycoside (acyl-D-galactoside uronate), and fatty acid soaps, and mixtures thereof.

Amphoteric and zwitterionic surfactants include betaines, N-alkylamidobetaines and derivatives thereof, proteins and derivatives thereof, glycine derivatives, sultaines, alkyl polyaminocarboxylates and alkylamphoacetates, and mixtures thereof.

Examples of thickeners include acrylamide polymers and copolymers, acrylate copolymers and salts thereof (such as sodium polyacrylate), xanthan gum and derivatives, cellulose gum and cellulose derivatives (such as methylcellulose, methylhydroxypropylcellulose, hydroxypropylcellulose, polypropylhydroxyethylcellulose), starch and starch derivatives (such as hydroxyethylamylose and starch amylase), polyoxyethylene, carbomer, hectorite and hectorite derivatives, sodium alginate, arabic gum, cassia gum, guar gum and guar gum derivatives, cocamide derivatives, alkyl alcohols, gelatin, PEG-derivatives, saccharides (such as fructose, glucose) and saccharides derivatives (such as PEG-120 methyl glucose diolate), and mixtures thereof.

Examples of water phase stabilizing agents include electrolytes (e.g. alkali metal salts and alkaline earth salts, especially the chloride, borate, citrate, and sulfate salts of sodium, potassium, calcium and magnesium, as well as aluminum chlorohydrate, and polyelectrolytes, especially hyaluronic acid and sodium hyaluronate), polyols (glycerine, propylene glycol, butylene glycol, and sorbitol), alcohols such as ethyl alcohol, and hydrocolloids, and mixtures thereof.

Examples of pH controlling agents include any water soluble acid such as a carboxylic acid or a mineral acid such as hydrochloric acid, sulphuric acid, and phosphoric acid, monocarboxylic acid such as acetic acid and lactic acid, and polycarboxylic acids such as succinic acid, adipic acid, citric acid, and mixtures thereof.

Example of preservatives and cosmetic biocides include paraben derivatives, hydantoin derivatives, chlorhexidine and its derivatives, imidazolidinyl urea, phenoxyethanol, silver derivatives, salicylate derivatives, triclosan, ciclopirox olamine, hexamidine, oxyquinoline and its derivatives, PVP-iodine, zinc salts and derivatives such as zinc pyrithione, and mixtures thereof.

Examples of sebum absorbants or sebum control agents include silica silylate, silica dimethyl silylate, dimethicone/vinyl dimethicone crosspolymer, polymethyl methacrylate, crosslinked methylmethacrylate, aluminum starch octenylsuccinate, and mixtures thereof.

Examples of vegetable or botanical extracts are derived from plants (herbs, roots, flowers, fruits, or seeds) in oil or water soluble form, such as coconut, green tea, white tea, black tea, horsetail, Ginkgo biloba, sunflower, wheat germ, seaweed, olive, grape, pomegranate, aloe, apricot kernel, apricot, carrot, tomato, tobacco, bean, potato, actzuki bean, catechu, orange, cucumber, avocado, watermelon, banana, lemon or palm. Examples of herbal extracts include dill, horseradish, oats, neem, beet, broccoli, tea, pumpkin, soybean, barley, walnut, flax, ginseng, poppy, avocado, pea, sesame, and mixtures thereof.

Examples of vitamins include a variety of different organic compounds such as alcohols, acids, sterols, and quinones. They may be classified into two solubility groups: lipid-soluble vitamins and water-soluble vitamins. Lipid-soluble vitamins that have utility in personal care formulations include retinol (vitamin A), ergocalciferol (vitamin D2), cholecalciferol (vitamin D3), phytonadione (vitamin K1), and tocopherol (vitamin E). Water-soluble vitamins that have utility in personal care formulations include ascorbic acid (vitamin C), thiamin (vitamin B1) niacin (nicotinic acid), niacinamide (vitamin B3), riboflavin (vitamin B2), pantothenic acid (vitamin B5), biotin, folic acid, pyridoxine (vitamin B6), and cyanocobalamin (vitamin B12). Additional examples of vitamins include derivatives of vitamins such as retinyl palmitate (vitamin A palmitate), retinyl acetate (vitamin A acetate), retinyl linoleate (vitamin A linoleate), and retinyl propionate (vitamin A propionate), tocopheryl acetate (vitamin E acetate), tocopheryl linoleate (vitamin E linoleate), tocopheryl succinate (vitamin E succinate), tocophereth-5, tocophereth-10, tocophereth-12, tocophereth-18, tocophereth-50 (ethoxylated vitamin E derivatives), PPG-2 tocophereth-5, PPG-5 tocophereth-2, PPG-10 tocophereth-30, PPG-20 tocophereth-50, PPG-30 tocophereth-70, PPG-70 tocophereth-100 (propoxylated and ethoxylated vitamin E derivatives), sodium tocopheryl phosphate, ascorbyl palmitate, ascorbyl dipalmitate, ascorbyl glucoside, ascorbyl tetraisopalmitate, tetrahexadecyl ascorbate, ascorbyl tocopheryl maleate, potassium ascorbyl tocopheryl phosphate, tocopheryl nicotinate, and mixtures thereof.

Examples of proteins or amino-acids and their derivatives include those extracted from wheat, soy, rice, corn, keratin, elastin or silk. Proteins may be in the hydrolysed form and they may also be quaternized, such as hydrolysed elastin, hydrolysed wheat powder, hydrolysed silk. Examples of protein include enzymes such as hydrolases, cutinases, oxidases, transferases, reductases, hemicellulases, esterases, isomerases, pectinases, lactases, peroxidases, laccases, catalases, and mixtures thereof. Examples of hydrolases include proteases (bacterial, fungal, acid, neutral or alkaline), amylases (alpha or beta), lipases, mannanases, cellulases, collagenases, lisozymes, superoxide dismutase, catalase, and mixtures thereof.

Examples of pigments and colorants include surface treated or untreated iron oxides, surface treated or untreated titanium dioxide, surface treated or untreated mica, silver oxide, silicates, chromium oxides, carotenoids, carbon black, ultramarines, chlorophyllin derivatives and yellow ocher. Examples of organic pigments include aromatic types including azo, indigoid, triphenylmethane, anthraquinone, and xanthine dyes which are designated as D&C and FD&C blues, browns, greens, oranges, reds, yellows, etc., and mixtures thereof. Surface treatments include those treatments based on lecithin, silicone, silanes, fluoro compounds, and mixtures thereof.

Examples of cosmetic fillers include talc, micas, kaolin, zinc or titanium oxides, calcium or magnesium carbonates, silica, silica silylate, titanium dioxide, glass or ceramic beads, polymethylmethacrylate beads, boron nitride, aluminum silicate, aluminum starch octenylsuccinate, bentonite, magnesium aluminum silicate, nylon, silk powder metal soaps derived from carboxylic acids having 8-22 carbon atoms, non-expanded synthetic polymer powders, expanded powders and powders from natural organic compounds, such as cereal starches, which may or may not be cross-linked, copolymer microspheres, polytrap, silicone resin microbeads, and mixtures thereof. The fillers may be surface treated to modify affinity or compatibility with remaining ingredients.

Examples of silicone conditioning agents include silicone oils such as dimethicone; silicone gums such as dimethiconol; silicone resins such as trimethylsiloxy silicate, polypropyl silsesquioxane; silicone elastomers; alkylmethylsiloxanes; organomodified silicone oils, such as amodimethicone, aminopropyl phenyl trimethicone, phenyl trimethicone, trimethyl pentaphenyl trisiloxane, silicone quaternium-16/glycidoxy dimethicone crosspolymer, silicone quaternium-16; saccharide functional siloxanes; carbinol functional siloxanes; silicone polyethers; siloxane copolymers (divinyldimethicone/dimethicone copolymer); acrylate or acrylic functional siloxanes; and mixtures or emulsions thereof.

Examples of cationic conditioning agents include guar derivatives such as hydroxypropyltrimethylammonium derivative of guar gum; cationic cellulose derivatives, cationic starch derivatives; quaternary nitrogen derivatives of cellulose ethers; homopolymers of dimethyldiallyl ammonium chloride; copolymers of acrylamide and dimethyldiallyl ammonium chloride; homopolymers or copolymers derived from acrylic acid or methacrylic acid which contain cationic nitrogen functional groups attached to the polymer by ester or amide linkages; polymeric quaternary ammonium salts of hydroxyethyl cellulose reacted with a fatty alkyl dimethyl ammonium substituted epoxide; polycondensation products of N,N'-bis-(2,3-epoxypropyl)-piperazine or piperazine-bis-acrylamide and piperazine; and copolymers of vinylpyrrolidone and acrylic acid esters with quaternary nitrogen functionality. Specific materials include the various polyquats Polyquaternium-7, Polyquaternium-8, Polyquaternium-10, Polyquaternium-11, and Polyquaternium-23. Other categories of conditioners include cationic surfactants such as cetyl trimethylammonium chloride, cetyl trimethylammonium bromide, stearyltrimethylammonium chloride, and mixtures thereof. In some instances, the cationic conditioning agent is also hydrophobically modified, such as hydrophobically modified quaternized hydroxyethylcellulose polymers; cationic hydrophobically modified galactomannan ether; and mixtures thereof.

Examples of hydrophobic conditioning agents include guar derivatives; galactomannan gum derivatives; cellulose derivatives; and mixtures thereof.

UV absorbers and sunscreen agents include those which absorb ultraviolet light between about 290-320 nanometers (the UV-B region) and those which absorb ultraviolet light in the range of 320-400 nanometers (the UV-A region).

Some examples of sunscreen agents are aminobenzoic acid, cinoxate, diethanolamine methoxycinnamate, digalloyl trioleate, dioxybenzone, ethyl 4-[bis(Hydroxypropyl)] aminobenzoate, glyceryl aminobenzoate, homosalate, lawsone with dihydroxyacetone, menthyl anthranilate, octocrylene, ethyl hexyl methoxycinnamate, octyl salicylate, oxybenzone, padimate O, phenylbenzimidazole sulfonic acid, red petrolatum, sulisobenzone, titanium dioxide, trolamine salicylate, and mixtures thereof.

Some examples of UV absorbers are acetaminosalol, allatoin PABA, benzalphthalide, benzophenone, benzophenone 1-12, 3-benzylidene camphor, benzylidenecamphor hydrolysed collagen sulfonamide, benzylidene camphor sulfonic Acid, benzyl salicylate, bornelone, bumetriozole, butyl Methoxydibenzoylmethane, butyl PABA, ceria/silica, ceria/silica talc, cinoxate, DEA-methoxycinnamate, dibenzoxazol naphthalene, di-t-butyl hydroxybenzylidene camphor, digalloyl trioleate, diisopropyl methyl cinnamate, dimethyl PABA ethyl cetearyldimonium tosylate, dioctyl butamido triazone, diphenyl carbomethoxy acetoxy naphthopyran, disodium bisethylphenyl tiamminotriazine stilbenedisulfonate, disodium distyrylbiphenyl triaminotriazine stilbenedisulfonate, disodium distyrylbiphenyl disulfonate, drometrizole, drometrizole trisiloxane, ethyl dihydroxypropyl PABA, ethyl diisopropylcinnamate, ethyl methoxycinnamate, ethyl PABA, ethyl urocanate, etrocrylene ferulic acid, glyceryl octanoate dimethoxycinnamate, glyceryl PABA, glycol salicylate, homosalate, isoamyl p-methoxycinnamate, isopropylbenzyl salicylate, isopropyl dibenzolylmethane, isopropyl methoxycinnamate, menthyl anthranilate, menthyl salicylate, 4-methylbenzylidene, camphor, octocrylene, octrizole, octyl dimethyl PABA, ethyl hexyl methoxycinnamate, octyl salicylate, octyl triazone, PABA, PEG-25 PABA, pentyl dimethyl PABA, phenylbenzimidazole sulfonic acid, polyacrylamidomethyl benzylidene camphor, potassium methoxycinnamate, potassium phenylbenzimidazole sulfonate, red petrolatum, sodium phenylbenzimidazole sulfonate, sodium urocanate, TEA-phenylbenzimidazole sulfonate, TEA-salicylate, terephthalylidene dicamphor sulfonic acid, titanium dioxide, tri-PABA panthenol, urocanic acid, VA/crotonates/methacryloxybenzophenone-1 copolymer, and mixtures thereof.

Examples of antidandruff agents include pyridinethione salts, selenium compounds such as selenium disulfide, and soluble antidandruff agents, and mixtures thereof.

Examples of antiperspirant agents and deodorant agents include aluminum chloride, aluminum zirconium tetrachlorohydrex GLY, aluminum zirconium tetrachlorohydrex PEG, aluminum chlorohydrex, aluminum zirconium tetrachlorohydrex PG, aluminum chlorohydrex PEG, aluminum zirconium trichlorohydrate, aluminum chlorohydrex PG, aluminum zirconium trichlorohydrex GLY, hexachlorophene, benzalkonium chloride, aluminum sesquichlorohydrate, sodium bicarbonate, aluminum sesquichlorohydrex PEG, chlorophyllin-copper complex, triclosan, aluminum zirconium octachlorohydrate, zinc ricinoleate, and mixtures thereof.

Examples of skin protectants include allantoin, aluminium acetate, aluminium hydroxide, aluminium sulfate, calamine, cocoa butter, cod liver oil, colloidal oatmeal, dimethicone, glycerin, kaolin, lanolin, mineral oil, petrolatum, shark liver oil, sodium bicarbonate, talc, witch hazel, zinc acetate, zinc carbonate, zinc oxide, and mixtures thereof.

Examples of hair dyes include 1-acetoxy-2-methylnaphthalene; acid dyes; 5-amino-4-chloro-o-cresol; 5-amino-2,6-dimethoxy-3-hydroxypyridine; 3-amino-2,6-dimethylphenol; 2-amino-5-ethylphenol HCl; 5-amino-4-fluoro-2-methylphenol sulfate; 2-amino-4-hydroxyethylaminoanisole; 2-amino-4-hydroxyethylaminoanisole sulfate; 2-amino-5-nitrophenol; 4-amino-2-nitrophenol; 4-amino-3-nitrophenol; 2-amino-4-nitrophenol sulfate; m-aminophenol HCl; p-aminophenol HCl; m-aminophenol; o-aminophenol; 4,6-bis(2-hydroxyethoxy)-m-phenylenediamine HCl; 2,6-bis(2-hydroxyethoxy)-3,5-pyridinediamine HCl; 2-chloro-6-ethylamino-4-nitrophenol; 2-chloro-5-nitro-N-hydroxyethyl p-phenylenediamine; 2-chloro-p-phenylenediamine; 3,4-diaminobenzoic acid; 4,5-diamino-1-((4-chlorophenyl)methyl)-1H-pyrazole-sulfate; 2,3-diaminodihydropyrazolo pyrazolone dimethosulfonate; 2,6-diaminopyridine; 2,6-diamino-3-((pyridin-3-yl)azo)pyridine; dihydroxyindole; dihydroxyindoline; N,N-dimethyl-p-phenylenediamine; 2,6-dimethyl-p-phenylenediamine; N,N-dimethyl-p-phenylenediamine sulfate; direct dyes; 4-ethoxy-m-phenylenediamine sulfate; 3-ethylamino-p-cresol sulfate; N-ethyl-3-nitro PABA; gluconamidopropyl aminopropyl dimethicone; Haematoxylon brasiletto wood extract; HC dyes; Lawsonia inermis (Henna) extract; hydroxyethyl-3,4-methylenedioxyaniline HCl; hydroxyethyl-2-nitro-p-toluidine; hydroxyethyl-p-phenylenediamine sulfate; 2-hydroxyethyl picramic acid; hydroxypyridinone; hydroxysuccinimidyl C21-22 isoalkyl acidate; isatin; Isatis tinctoria leaf powder; 2-methoxymethyl-p-phenylenediamine sulfate; 2-methoxy-p-phenylenediamine sulfate; 6-methoxy-2,3-pyridinediamine HCl; 4-methylbenzyl 4,5-diamino pyrazole sulfate; 2,2'-methylenebis 4-aminophenol; 2,2'-methylenebis-4-aminophenol HCl; 3,4-methylenedioxyaniline; 2-methylresorcinol; methylrosanilinium chloride; 1,5-naphthalenediol; 1,7-naphthalenediol; 3-nitro-p-Cresol; 2-nitro-5-glyceryl methylaniline; 4-nitroguaiacol; 3-nitro-p-hydroxyethylaminophenol; 2-nitro-N-hydroxyethyl-p-anisidine; nitrophenol; 4-nitrophenyl aminoethylurea; 4-nitro-o-phenylenediamine dihydrochloride; 2-nitro-p-phenylenediamine dihydrochloride; 4-nitro-o-phenylenediamine HCl; 4-nitro-m-phenylenediamine; 4-nitro-o-phenylenediamine; 2-nitro-p-phenylenediamine; 4-nitro-m-phenylenediamine sulfate; 4-nitro-o-phenylenediamine sulfate; 2-nitro-p-phenylenediamine sulfate; 6-nitro-2,5-pyridinediamine; 6-nitro-o-toluidine; PEG-3 2,2'-di-p-phenylenediamine; p-phenylenediamine HCl; p-phenylenediamine sulfate; phenyl methyl pyrazolone; N-phenyl-p-phenylenediamine HCl; pigment blue 15:1; pigment violet 23; pigment yellow 13; pyrocatechol; pyrogallol; resorcinol; sodium picramate; sodium sulfanilate; solvent yellow 85; solvent yellow 172; tetraaminopyrimidine sulfate; tetrabromophenol blue; 2,5,6-triamino-4-pyrimidinol sulfate; 1,2,4-trihydroxybenzene.

Example of nail care ingredients include butyl acetate; ethyl acetate; nitrocellulose; acetyl tributyl citrate; isopropyl alcohol; adipic acid/neopentyl glycol/trimelitic anhydride copolymer; stearalkonium bentonite; acrylates copolymer; calcium pantothenate; Cetraria islandica extract; Chondrus crispus; styrene/acrylates copolymer; trimethylpentanediyl dibenzoate-1; polyvinyl butyral; N-butyl alcohol; propylene glycol; butylene glycol; mica; silica; tin oxide; calcium borosilicate; synthetic fluorphlogopite; polyethylene terephtalate; sorbitan laurate derivatives; talc; jojoba extract; diamond powder; isobutylphenoxy epoxy resin; silk powder; and mixtures thereof.

Examples of fragrances or perfume include hexyl cinnamic aldehyde; anisaldehyde; methyl-2-n-hexyl-3-oxo-cyclopentane carboxylate; dodecalactone gamma; methylphenylcarbinyl acetate; 4-acetyl-6-tert-butyl-1, 1-dimethyl indane; patchouli; olibanum resinoid; labdanum; vetivert; copaiba balsam; fir balsam; 4-(4-hydroxy-4-methyl pentyl)-3-cyclohexene-1-carboxaldehyde; methyl anthranilate; geraniol; geranyl acetate; linalool; citronellol; terpinyl acetate; benzyl salicylate; 2-methyl-3-(p-isopropylphenyl)-propanal; phenoxyethyl isobutyrate; cedryl acetal; aubepine; musk fragrances; macrocyclic ketones; macrolactone musk fragrances; ethylene brassylate; and mixtures thereof. Further perfume ingredients are described in detail in standard textbook references such as *Perfume and Flavour Chemicals,* 1969, S. Arctander, Montclair, N.J.

Examples of antioxidants are acetyl cysteine, arbutin, ascorbic acid, ascorbic acid polypeptide, ascorbyl dipalmitate, ascorbyl methylsilanol pectinate, ascorbyl palmitate, ascorbyl stearate, BHA, p-hydroxyanisole, BHT, t-butyl hydroquinone, caffeic acid, Camellia sinensis Oil, chitosan ascorbate, chitosan glycolate, chitosan salicylate, chlorogenic acids, cysteine, cysteine HCl, decyl mercaptomethylimidazole, erythorbic acid, diamylhydroquinone, di-t-butylhydroquinone, dicetyl thiodipropionate, dicyclopentadiene/t-butylcresol copolymer, digalloyl trioleate, dilauryl thiodipropionate, dimyristyl thiodipropionate, dioleyl tocopheryl methylsilanol, isoquercitrin, diosmine, disodium ascorbyl sulfate, disodium rutinyl disulfate, distearyl thiodipropionate, ditridecyl thiodipropionate, dodecyl gallate, ethyl ferulate, ferulic acid, hydroquinone, hydroxylamine HCl, hydroxylamine sulfate, isooctyl thioglycolate, kojic acid, madecassicoside, magnesium ascorbate, magnesium ascorbyl phosphate, melatonin, methoxy-PEG-7 rutinyl succinate, methylene di-t-butylcresol, methylsilanol ascorbate, nordihydroguaiaretic acid, octyl gallate, phenylthioglycolic acid, phloroglucinol, potassium ascorbyl tocopheryl phosphate, thiodiglycolamide, potassium sulfite, propyl gallate, rosmarinic acid, rutin, sodium ascorbate, sodium ascorbyl/cholesteryl phosphate, sodium bisulfite, sodium erythorbate, sodium metabisulfide, sodium sulfite, sodium thioglycolate, sorbityl furfural, tea tree (Melaleuca aftemifolia) oil, tocopheryl acetate, tetrahexyldecyl ascorbate, tetrahydrodiferuloylmethane, tocopheryl linoleate/oleate, thiodiglycol, tocopheryl succinate, thiodiglycolic acid, thioglycolic acid, thiolactic acid, thiosalicylic acid, thiotaurine, retinol, tocophereth-5, tocophereth-10, tocophereth-12, tocophereth-18, tocophereth-50, tocopherol, tocophersolan, tocopheryl linoleate, tocopheryl nicotinate, tocoquinone, o-tolyl biguanide, tris(nonylphenyl) phosphite, ubiquinone, zinc dibutyldithiocarbamate, and mixtures thereof.

Examples of oxidizing agents are ammonium persulfate, calcium peroxide, hydrogen peroxide, magnesium peroxide, melamine peroxide, potassium bromate, potassium caroate, potassium chlorate, potassium persulfate, sodium bromate, sodium carbonate peroxide, sodium chlorate, sodium iodate, sodium perborate, sodium persulfate, strontium dioxide, strontium peroxide, urea peroxide, zinc peroxide, and mixtures thereof.

Examples of reducing agents are ammonium bisufite, ammonium sulfite, ammonium thioglycolate, ammonium thiolactate, cystemaine HCl, cystein, cysteine HCl, ethanolamine thioglycolate, glutathione, glyceryl thioglycolate, glyceryl thioproprionate, hydroquinone, p-hydroxyanisole, isooctyl thioglycolate, magnesium thioglycolate, mercaptopropionic acid, potassium metabisulfite, potassium sulfite, potassium thioglycolate, sodium bisulfite, sodium hydrosulfite, sodium hydroxymethane sulfonate, sodium metabisulfite, sodium sulfite, sodium thioglycolate, strontium thioglycolate, superoxide dismutase, thioglycerin, thioglycolic acid, thiolactic acid, thiosalicylic acid, zinc formaldehyde sulfoxylate, and mixtures thereof.

Examples of propellant gases include carbon dioxide, nitrogen, nitrous oxide, volatile hydrocarbons such as butane, isobutane, or propane, and chlorinated or fluorinated hydrocarbons such as dichlorodifluoromethane and dichlorotetrafluoroethane or dimethylether; and mixtures thereof.

Examples of film formers include those polymers capable, by themselves or in the presence of an auxiliary film-forming agent, of forming a macroscopically continuous film on a support, especially on keratin materials, preferably a cohesive film and better still a film whose cohesion and mechanical properties are such that the said film can be isolated from the said support.

Examples of antiacne agents include salicylic acid, sulfur benzoyl, peroxide, tretinoin, and mixtures thereof.

Examples of antibacterial agents include chlorohexadiene gluconate, alcohol, benzalkonium chloride, benzethonium chloride, hydrogen peroxide, methylbenzethonium chloride, phenol, poloxamer 188, povidone-iodine, and mixtures thereof.

Examples of antifungal agents include miconazole nitrate, calcium undecylenate, undecylenic acid, zinc undecylenate, and mixtures thereof.

Examples of therapeutic active agents include penicillins, cephalosporins, tetracyclines, macrolides, epinephrine, amphetamines, aspirin, acetaminophen, barbiturates, catecholamines, benzodiazepine, thiopental, codeine, morphine, procaine, lidocaine, benzocaine, sulphonamides, ticonazole, perbuterol, furosamide, prazosin, hormones, prostaglandins, carbenicillin, salbutamol, haloperidol, suramin, indomethicane, diclofenac, glafenine, dipyridamole, theophylline, hydrocortisone, steroids, scopolamine, and mixtures thereof.

Examples of external analgesics are benzyl alcohol, capsicum oleoresin (Capsicum frutescens oleoresin), methyl salicylate, camphor, phenol, capsaicin, juniper tar (Juniperus oxycedrus tar), phenolate sodium (sodium phenoxide), capsicum (Capsicum frutescens), menthol, resorcinol, methyl nicotinate, turpentine oil (turpentine), and mixtures thereof.

An example of a skin bleaching agent is hydroquinone.

Examples of anti-cancer agents include alkylating agents (such as busulfan, fluorodopan), antimitotic agents (such as colchicine, rhizoxin), topoisomerase I inhibitors (such as camptothecin and its derivatives), topoisomerase II inhibitors (such as menogaril, amonafide), RNA/DNA or DNA anti-metabolites (such as acivicin, guuanazole), plant alkaloids and terpenoids, antineoplastics, some plant-derived compounds (such as podophyllotoxin, vinca alkaloids), and mixtures thereof.

Examples of diuretics include loop diuretics (such as bumetanide, furosemide), thiazide diuretics (such as chlorothiazide, hydroflumethiazide), potassium-sparing diuretics (such as amioloride, spironolactone), carbonic anhydrase inhibitors (such as acetazolamide), osmotic diuretics (such as mannitol), and mixtures thereof.

Examples of agents for treating gastric and duodenal ulcers include proton pump inhibitor (such as lansoprazole, omeprazole), acid blockers or H2 histamine blockers (such as cimetidine, ranitidine), bismuth, sucralfate, and mixtures thereof.

Examples of proteolytic enzymes include nattokinase, serratiopeptidase, bromelain, papain, and mixtures thereof.

Examples of antihistamine or H1 histamine blockers include brompheniramine, clemastine, cetirizine, loratadine, fexofenadine, and mixtures thereof.

Examples of sedatives include barbiturates (such as phenobarbitol), benzodiazepines (such as lorazepam), herbal sedatives, benzodiazepine-like drugs (such as zolpidem, zopiclone), and mixtures thereof.

Examples of bronchodilators include short-acting β2-agonists and long-acting β2-agonists, anticholinergics, and mixtures thereof.

Examples of diluents include those discussed previously. The diluent in the cosmetic composition may be the same or may be different from the diluent used in the manufacture of the silicone based material cured via condensation cure chemistry discussed previously.

Further materials suitable for the personal care and health care are well known to the person skilled in the art and are described in many text books as well as other publications.

The general level of material in the cosmetic compositions may vary from 0.1% to 80% by weight, alternatively from 0.1% to 10%, alternatively from 0.5% to 5%, relative to the total weight of the cosmetic composition. The cosmetic ingredient is present at a level of from 0.01% to 99.99% by weight, relative to the total weight of the cosmetic composition. The cosmetic ingredient may be a mixture of cosmetic ingredients as listed above.

In some instances, the material is used in conjunction with a cosmetic ingredient selected from a cationic conditioning agent, a hydrophobic conditioning agent, or mixtures thereof, in a cosmetically acceptable medium.

The cosmetic composition may be prepared by a process comprising the steps of
i. Mixing a silicone material
ii. and at least one cosmetic ingredient,
iii. optionally in the presence of a cosmetically acceptable medium.

The cosmetic compositions may be prepared by mixing the silicone based material in the appropriate phase of the final cosmetic composition.

When the silicone based material is used in its neat form, it may be added in the hydrophobic phase. In some events, the hydrophobic phase may be a single phase, that is, a monophasic system, or anhydrous system. In some events, a second hydrophilic or aqueous phase may be mixed with the hydrophobic phase to provide for a dispersion or emulsion.

When the silicone based material is used in emulsion form, it may be mixed with the aqueous phase ingredients and optionally subsequently mixed with an optional second hydrophobic phase. When there are multiple phases, the different phases may subsequently be mixed together, optionally under heating.

The process may be conducted at temperatures ranging of from 15 to 90° C., alternatively of from 20 to 60° C., alternatively at room temperature (25° C.), using simple propeller mixers, counter-rotating mixers, or homogenizing mixers. No special equipment or processing conditions are typically required. Depending on the type of composition prepared, the method of preparation will be different, but such methods are well known in the art.

The cosmetic compositions may be in the form of a cream, a gel, a powder (free flowing powder or pressed), a paste, a solid, freely pourable liquid, an aerosol. The cosmetic compositions may be in the form of monophasic systems, biphasic or alternate multiphasic systems; emulsions, e.g. oil-in-water, water-in-oil, silicone-in-water, water-in-silicone; multiple emulsions, e.g. oil-in-water-in-oil, polyol-in-silicone-in-water, oil-in-water-in-silicone.

Skin care compositions include shower gels, soaps, hydrogels, creams, lotions and balms; antiperspirants; deodorants such as sticks, soft solid, roll on, aerosol, and pump sprays; skin creams; skin care lotions; moisturizers; facial treatments such as wrinkle control or diminishment treatments; exfoliates; body and facial cleansers; bath oils; perfumes; colognes; sachets; sunscreens; mousses; pre-shave and after-shave lotions; shaving soaps; shaving lathers; depilatories; make-ups; color cosmetics; foundations; concealers; blushes; lipsticks; eyeliners; mascaras; oil removers; color cosmetic removers, powders, and kits thereof. Skin care compositions exclude patches.

Hair care compositions include shampoos, rinse-off conditioners, leave-in conditioners and styling aids, gels, sprays, pomades, mousses, waxes, cuticle coats, hair colorants, hair relaxants, hair straighteners, permanents, and kits thereof.

Nail care compositions include color coats, base coats, nail hardeners, and kits thereof.

Health care compositions may be in the form of ointments, creams, gels, mousses, pastes, spray on bandages, foams and/or aerosols or the like, medicament creams, pastes or sprays including anti-acne, dental hygienic, antibiotic, healing promotive, which may be preventative and/or therapeutic medicaments, and kits thereof. Health care compositions exclude patches.

The cosmetic compositions may be used by the standard methods, such as applying them to the human or animal body, e.g. skin or hair, using applicators, brushes, applying by hand, pouring them and/or possibly rubbing or massaging the composition onto or into the body. Removal methods, for example for colour cosmetics are also well known standard methods, including washing, wiping, scrubbing and the like.

The invention also comprises a method of treating keratinous substrates, such as hair or skin, by applying to it a cosmetic composition according to the first aspect of the invention.

The cosmetic compositions may be used on hair in a conventional manner. An effective amount of the composition for washing or conditioning hair is applied to the hair. Such effective amounts generally range from about 1 g to about 50 g, preferably from about 1 g to about 20 g. Application to the hair typically includes working the cosmetic composition through the hair such that most or all of the hair is contacted with the cosmetic composition. These steps can be repeated as many times as desired to achieve the desired benefit.

Benefits obtained from using the cosmetic compositions on hair include one or more of the following benefits: hair conditioning, softness, detangling ease, silicone deposition, anti-static, anti-frizz, lubricity, shine, strengthening, viscosity, tactile, wet combing, dry combing, improvement in coloration process, color retention, straightening, heat protection, styling, or curl retention.

The cosmetic compositions may be used on skin in a conventional manner. An effective amount of the composition for the purpose is applied to the skin. Such effective amounts generally range from about 1 $mg/cm^2$ to about 3 $mg/cm^2$. Application to the skin typically includes working the cosmetic composition into the skin. This method for applying to the skin comprises the steps of contacting the skin with the cosmetic composition in an effective amount and then rubbing the composition into the skin. These steps can be repeated as many times as desired to achieve the desired benefit.

Benefits obtained from using the cosmetic compositions on skin include one or more of the following benefits: skin softness, suppleness, moisturisation, skin feel, foam generation, durability, substantivity, long lasting, long wear, shine or mattifying effect, SPF boost, pollutants barrier.

The invention thus also comprises a process to care for keratinous substrates, such as hair or skin, by applying to it a cosmetic composition according to the first aspect of the invention.

The process to care for keratinous substrates comprises the steps of
a. Providing for a cosmetic composition comprising silicone material cured via a condensation cure chemistry and at least one cosmetic ingredient, optionally in a cosmetically acceptable medium,
b. Applying the composition to the keratinous substrate
c. Optionally rinsing.

The optional standing time of the process of caring or conditioning keratinous fibres may range of from 10 seconds to 1 hour, alternatively of from 30 seconds to 30 minutes, alternatively of from 30 seconds to 10 minutes.

In one embodiment, the present invention provides for the use of the present cosmetic composition to care for keratinous substrates, that is to cleanse, to condition, to refresh, to make up, to remove make up, to fix hair.

EXAMPLES

The following examples are included to demonstrate preferred embodiments of the invention. Unless otherwise indicated, all recipes are in mass parts, therefore the sum is not necessarily 100.

Examples of Silicone Based Gel Cured Via a Condensation Cure CHEMISTRY (G)=Example Materials Unless stated otherwise, all experiments were made at ambient conditions, that is temperature of 23° C.±1° and approx. 30% relative humidity. All numbers relating to the condensation cure composition are mass parts.

Typically 80-90 g of condensation cure silicone based material cured via a condensation cure chemistry are prepared using the following protocol: the linear OH-terminated polydimethyl siloxane(s) was mixed with the cross-linker (x-linker) and with the optional diluent, using a speed mixer DAC 150.1 FV (available from Hauschield, Germany) at 3000 RPM for 30 s. The catalyst, typically tetra-butyl titanate (TNBT), was then added and the mixture was stirred again for 90 seconds at maximum speed using the same device. Thus obtained material was left in an open container at ambient conditions for 1 to 3 weeks to allow for full cure. Unless stated otherwise all compositions were crystal clear polymers or gels.

Cure was characterized using a TA.XT Plus Texture Analyser, available from Texture Technologies and equipped with rounded-end plastic probe. The latter was approached to the surface of the cure material at given speed until reaching certain penetration depth. At maximum penetration (in this case 5 mm), one records the maximal positive force, hereafter abbreviated as F(+). The higher F(+) the harder the material. The probe is then retracted until it is fully detached from the material. During retraction, the maximum adhesion force is measured. The adhesion force is abbreviated hereafter as F(−). With the onset of cure, the F(+) starts to increase and reaches a plateau when fully cured. The cure is deemed completed when the time variation in F(+) is less than 15%. The lower the F(+) the more flowable the material. The integration of the F(−) curve produces the adhesion energy. The value is standardly calculated by the software of the instrument. The higher the absolute value the stronger the adhesion.

Particularly interesting are materials which present the combination of F(+) below 10 g, F(−) in the interval −1 g to −10 g and adhesion energy in the domain −200 to −80. These materials are characterized with high stringiness and ability to form filaments; said filaments detach cleanly from the probe.

For the purpose of this invention, "flowable" is defined as follows: the condensation cure silicone based material is prepared in a shallow aluminium dish (ca 5 cm in diameter, 1 cm depth). Upon full cure, the dish is held inclined at an angle of 90° C. with respect to its normal orientation approximately 15 cm above the lab balance, and the material is allowed to flow. The time (t(flow)) to pour (as measured by the balance) 1 g of cured material has been measured. When t(flow) is less than 3 minutes, the material is deemed flowable. Obviously more flowable materials are characterized by lower t(flow). Less flowable material are deemed useful in the scope of the present invention, as long as their handling allows for dispersion and miscibility with other ingredients of the cosmetic composition.

Following abbreviations are used in the tables below:

Polymer type 1: α,ω-Dihydroxy polydimethyl siloxane with viscosity at 23° C. of 2,000 mPa·s (viscosity measured using a Brookfield cone plate viscometer RV DIII using a cone plate CP-52 at 20 rpm), Mn of 22,000, SiOH content=2*100*1000/22000=9.09 mmol/100 g Polymer type 5: α,ω-Dihydroxy polydimethyl siloxane with viscosity at 23° C. of 13,500 mPa·s (viscosity measured using a Brookfield cone plate viscometer RV DIII using a cone plate CP-52 at 5 rpm), Mn of 43,000, SiOH content=2*100*1000/43000=4.65 mmol/100 g Polymer type P: α,ω-Dihydroxy polydimethyl siloxane with viscosity at 23° C. of 50,000 mPa·s (viscosity measured using a Brookfield cone plate viscometer RV DIII using a cone plate CP-52 at 0.55 rpm), Mn of 63,000, SiOH content=2*100*1000/63000=3.17 mmol/100 g TEOS: tetraethoxy silane X-linker E: W—B—W type polymer where W is $(EtO)_3$—Si-D-, B is $[SiO_2(CH_3)_2]_{800-900}$, D is $C_2H_4$. This material has a viscosity at 23° C. of 50,000 mPa·s (viscosity measured using a Brookfield cone plate viscometer RV DIII using a cone plate CP-52 at 3 rpm), Mn of 66,000

TNBT=tetra n-butyl titanate, commercially available as Tyzor® TNBT from Dorf Ketal Diluent (where used) were abbreviated as follows:

200 fluid 5 cSt: trimethyl end-capped polydimethyl siloxane with viscosity of 5 cSt at 23° C. commercially available from Dow Corning under the trade name Dow Corning® 200 fluid 5 cSt (about 5 mPa·s)

200 fluid 2 cSt: trimethyl end-capped polydimethyl siloxane with viscosity of 2 cSt at 23° C. commercially available from Dow Corning under the trade name Dow Corning® 200 fluid 2 sct. This material is volatile and when used as diluent the inventors have topped-up the material with the amount of evaporated diluent on a daily basis.

200 fluid 100 cSt: trimethyl end-capped polydimethyl siloxane with viscosity of 100 cSt at 23° C. commercially available from Dow Corning under the trade name Dow Corning® 200 fluid 100 cSt (about 100 mPa·s)

Lytol: light mineral oil commercially available as Lytol™ from Sonneborn.

Example materials 1 to 4 are disclosed in Table 1.

TABLE 1

| Reactant | Example material 1 | Example material 2 | Example material 3 | Example material 4 |
|---|---|---|---|---|
| polymer type 1 | 100.00 | 100.00 | — | — |
| polymer type 5 | — | — | 100.00 | 100.00 |
| TEOS | 1.00 | 1.00 | 0.51 | 0.51 |
| TNBT | 0.20 | 0.20 | 0.11 | 0.11 |
| 200 fluid* 5 cSt | — | 100.00 | — | 100.00 |
| F(+)- after 3 weeks [g] | 521.7 | 13.0 | 533.4 | 2.6 |
| F(−) after 3 weeks [g] | −52.0 | −5.4 | −151.4 | −2.6 |
| t(flow) | >5 min | >5 min | >5 min | >5 min |

Example materials 5 to 8 are disclosed in Table 2.

TABLE 2

| Reactant | Example material 5 | Example material 6 | Example material 7 | Example material 8 |
|---|---|---|---|---|
| X-linker E | 150.00 | 300.00 | 150.00 | 150.00 |
| polymer type 1 | — | — | 74.50 | 74.50 |
| polymer type 5 | 146.00 | 146.00 | — | — |
| TNBT | 0.15 | 0.15 | 0.15 | 0.15 |
| 200 fluid* 5 cSt | — | 250.00 | — | 250.00 |
| F(+)- after 3 weeks [g] | 964.7 | 113.4 | 1581.5 | 115.4 |
| F(−) after 3 weeks [g] | −21.5 | −8.3 | −33.7 | −8.1 |
| t(flow) | >5 min | >5 min | >5 min | >5 min |

Example materials 9 to 14 are disclosed in Table 3.

TABLE 3

| Reactant | Example material 9 | Example material 10 | Example material 11 | Example material 12 | Example material 13 | Example material 14 |
| --- | --- | --- | --- | --- | --- | --- |
| X-linker E | 10.00 | 5.00 | 20.00 | 10.00 | 30.00 | 15.00 |
| polymer type 5 | 100.00 | 100.00 | 100.00 | 100.00 | 100.00 | 100.00 |
| TNBT | 0.10 | 0.10 | 0.20 | 0.20 | 0.25 | 0.25 |
| 200 fluid* 5 cSt | — | — | 100.00 | 100.00 | 200.00 | 200.00 |
| F(+)- after 3 weeks [g] | 4.6 | 2.0 | 2.3 | 1.1 | 2.3 | 1.2 |
| F(−) after 3 weeks [g] | −3.6 | −2.4 | −2.5 | −2.6 | −5.1 | −2.6 |
| Adhesion energy after 3 weeks (AU) | | | | 0.1 | 167 | 0.0 |
| t(flow) | | | 2 min 35 sec | 25 sec | >3 min | |

Example materials 15 to 17 are disclosed in Table 4.

TABLE 4

| Reactant | Example material 15 | Example material 16 | Example material 17 |
| --- | --- | --- | --- |
| X-linker E | 10.00 | 20.00 | 30.00 |
| polymer type P | 200.00 | 200.00 | 200.00 |
| TNBT | 0.20 | 0.25 | 0.30 |
| 200 fluid* 5 cSt | — | 200.00 | 400.00 |
| F(+)- after 3 weeks [g] | 7.7 | 1.2 | 1.2 |
| F(−) after 3 weeks [g] | −6.5 | −2.6 | −2.6 |
| Adhesion energy after 3 weeks (AU) | 98 | 0.1 | 0.1 |
| t(flow) | — | — | 4 sec |

Example materials 18 to 23 are disclosed in Table 5.

TABLE 5

| Reactant | Example material 18 | Example material 19 | Example material 20 | Example material 21 | Example material 22 | Example material 23 |
| --- | --- | --- | --- | --- | --- | --- |
| X-linker E | 50.00 | 20.00 | 100.00 | 40.00 | 150.00 | 60.00 |
| polymer type 5 | 100.00 | 100.00 | 100.00 | 100.00 | 100.00 | 100.00 |
| TNBT | 0.11 | 0.11 | 0.20 | 0.20 | 0.25 | 0.25 |
| 200 fluid* 5 cSt | — | — | 100.00 | 100.00 | 200.00 | 200.00 |
| F(+)- after 3 weeks [g] | 311.1 | 24.5 | 165.3 | 24.9 | 61.8 | 24.6 |
| F(−) after 3 weeks [g] | −38.6 | −34.2 | −10.5 | −14.2 | −6.9 | −5.5 |
| Adhesion energy after 3 weeks (AU) | 67.8 | 27.3 | 14.0 | 71.3 | 12.2 | 14.6 |

Example materials 24 to 26 are disclosed in Table 6.

TABLE 6

| Reactant | Example material 24 | Example material 25 | Example material 26 |
| --- | --- | --- | --- |
| X-linker E | 20.00 | 40.00 | 60.00 |
| polymer type P | 200.00 | 200.00 | 200.00 |
| TNBT | 0.20 | 0.25 | 0.35 |
| 200 fluid* 5 cSt | — | 200.00 | 400.00 |
| F(+)- after 3 weeks [g] | 17.5 | 4.1 | 3.9 |
| F(−) after 3 weeks [g] | −15.3 | −7.0 | −5.8 |
| Adhesion energy after 3 weeks (AU) | 718 | 218 | 60 |

Example materials 27 to 29 are disclosed in Table 7.

TABLE 7

| Reactant | Example material 27 | Example material 28 | Example material 29 |
| --- | --- | --- | --- |
| X-linker E | 100.00 | 300.00 | 226.30 |
| polymer type 5 | 100.00 | 100.00 | 100.00 |
| TNBT | 0.20 | 0.20 | 0.35 |
| 200 fluid, 5 cSt | 200.00 | 200.00 | 300.00 |
| F(+)- after 3 weeks [g] | 6.4 | 1.1 | 1.4 |
| F(−) after 3 weeks [g] | −6.4 | −2.7 | −3.6 |
| Adhesion energy after 3 weeks (AU) | 34.6 | 22.8 | 0.1 |

Example materials 30 to 35 are disclosed in Table 8.

TABLE 8

| Reactant | Example material 30 | Example material 31 | Example material 32 | Example material 33 | Example material 34 | Example material 35 |
|---|---|---|---|---|---|---|
| X-linker E | 20.00 | 40.00 | 30.00 | 60.00 | 100.00 | 300.00 |
| polymer type 5 | 100.00 | 100.00 | 100.00 | 100.00 | 100.00 | 100.00 |
| TNBT | 0.20 | 0.20 | 0.25 | 0.25 | 0.20 | 0.25 |
| LYTOL | 100.00 | 100.00 | 200.00 | 200.00 | 200.00 | 200.00 |
| F(+)- after 3 weeks [g] | 1.8 | 18.2 | 3.5 | 23.0 | 1.6 | 1.1 |
| F(−) after 3 weeks [g] | −2.4 | −11.7 | −4.5 | −4.2 | −4.2 | −2.7 |
| t(flow), min | >2 min 40 sec | — | — | >5 min | — | — |
| Adhesion energy after 3 weeks (AU) | 0.1 | 67.7 | 318 | 17 | 73.7 | 0.1 |
| Appearance | — | — | Turbid | Turbid | — | — |

Example materials 36 to 38 are disclosed in Table 9.

TABLE 9

| Reactant | Example material 36 | Example material 37 | Example material 38 |
|---|---|---|---|
| X-linker E | 100.00 | 300.00 | 226.30 |
| polymer type 5 | 100.00 | 100.00 | 100.00 |
| TNBT | 0.20 | 0.20 | 0.35 |
| 200 fluid, 100 cSt | 200.00 | 200.00 | 300.00 |
| F(+)- after 3 weeks [g] | 80.927 | 61.8 | 220.2 |
| F(−) after 3 weeks [g] | −6.077 | −24.1 | −5.1 |

Example materials 39 to 44 are disclosed in Table 10.

TABLE 10

| Reactant | Example material 39 | Example material 40 | Example material 41 | Example material 42 | Example material 43 | Example material 44 |
|---|---|---|---|---|---|---|
| X-linker E |  | 30.0 | 15.0 | 30.0 | 40.0 | 60.0 |
| polymer type 5 | 100.00 | 100.00 | 100.00 |  |  |  |
| polymer type P |  |  |  | 200.00 | 200.00 | 200.00 |
| TEOS | 0.51 |  |  |  |  |  |
| TNBT | 0.11 | 0.25 | 0.25 | 0.30 | 0.25 | 0.35 |
| 200 fluid, 2 cst | 100.00 | 200.00 | 200.00 | 400.00 | 200.00 | 400.00 |
| F(+)- after 3 weeks [g] |  | 3.4 | 1.1 | 1.2 | 8.8 |  |
| F(−) after 3 weeks [g] |  | −6.6 | −2.5 | −2.6 | −12.4 |  |
| Adhesion (AU) after 3 weeks |  | 168 | 0.1 | 0.1 | 154 |  |

The evolution of the material properties of selected example materials are shown in Table 11.

TABLE 11

| | Example material 15 | Example material 17 | Example material 19 |
|---|---|---|---|
| F(+) day 0 | 1.0 | 1.1 | 1.0 |
| F(−) day 0 | −1.2 | −1.0 | 1.4 |
| Adhesion energy, Day 0 | 0.1 | 0.1 | 0.1 |
| F(+) day 7 | 2.2 | 2.0 | 7.2 |
| F(−) day 7 | −2.4 | −3.7 | −5.8 |
| Adhesion energy, Day 7 | 0.1 | 78.6 | 83.6 |
| F(+) day 14 | 2.3 | 2.3 | 7.5 |
| F(−) day 14 | −3.2 | −5.0 | −6.2 |
| Adhesion energy, Day 14 | −204.0 | −138.5 | −102.2 |
| F(+) day 21 | 2.3 | 2.3 | 7.7 |
| F(−) day 21 | −2.5 | −5.1 | −6.5 |
| Adhesion energy, Day 21 | 0.1 | 167.0 | 98.0 |
| F(+) day 28 | 2.5 | 2.5 | 7.7 |
| F(−) day 28 | −2.4 | −5.3 | −6.4 |
| Adhesion energy, Day 28 | 0.1 | 219.6 | 100.8 |
| F(+) day + 1 year | 3.7 | 2.5 | 12.8 |
| F(−) day + 1 year | −3.0 | −3.7 | −9.7 |
| Adhesion energy, +1 year | 15 | 240 | 132 |

COSMETIC COMPOSITION EXAMPLES

Example 1: Oil in Water Sun Screen Cream

| Ingredients of Composition 1 | % wt |
|---|---|
| Phase A | |
| Butyl Methoxydibenzoylmethane | 3.0 |
| Octocrylene | 3.6 |
| Ethylhexyl Methoxycinnamate | 5.0 |
| Ethylhexyl Salicylate | 5.0 |
| Phase B | |
| Isohexadecane | 5.0 |
| Trimethylsiloxysilicate (and) Polypropylsilsesquioxane | 1.0 |
| Caprylyl Methicone | 4.4 |

| Ingredients of Composition 1 | % wt |
|---|---|
| PEG-12 Dimethicone | 4.0 |
| Example material 12 | 3.0 |
| Phase C | |
| Decyl Glucoside | 0.5 |
| Glycerin | 5.0 |
| Deionized Water | 58.5 |
| Phase D | |
| Polyacrylamide (and) C13-14 Isoparaffin (and) Laureth-7 | 2.0 |

Procedure to prepare the Oil in Water sun screen cream of Example 1:

1. Mix phase A ingredients together and heat to 60° C. until homogeneous.
2. Cool down to room temperature.
3. Mix Phase B ingredients until homogeneous
4. Add phase A to phase B mixing until homogeneous.
5. Mix phase C ingredients together.
6. Add mixture of phase A and B to phase C under agitation.
7. Add phase D to mixture (A+B+C). Mix until homogeneous.

In such sunscreen compositions, the sun filters and emollients may be replaced by any typical of such sunfilters and emollients as best suits the formulation requirements for sun protection and/or sensory feel.

Example 2: Foaming Cleanser

| | Ingredients of Example 2 | % wt |
|---|---|---|
| | Phase A | |
| 1 | *Simmondsia Chinensis* (Jojoba) Seed Oil | 1.0 |
| 2 | Sodium Laureth Sulfate | 6.0 |
| 3 | Cocamidopropyl Hydroxysultaine | 3.0 |
| 4 | Decyl Glucoside | 5.0 |
| 5 | Example material 11 | 8.0 |
| | Phase B | |
| 5 | Acrylates Copolymer | 8.0 |
| 6 | *Rubus Idaeus* (Raspberry) Fruit Water | 20.0 |
| 7 | Distilled Water | To 100.0% wt |
| | Phase C | |
| 8 | Sodium Hydroxide (10% wt solution in water) | 1.7 |
| | Phase D | |
| 9 | Chitosan Succinamide | 1.0 |
| 10 | Propylene Glycol (and) Diazolidinyl Urea (and) Methylparaben (and) Propylparaben | q.s. |

Procedure to prepare the foaming cleanser of Example 2:

1. Mix Phase B ingredients together.
2. Add ingredient 2 with mixing.
3. Add ingredient 8 with mixing.
4. Add ingredients 1, 3, 4 and 5 with mixing.
5. Add ingredients 9 and 10 and mix.

Example 3: O/W Foundation

| | Ingredients of Example 3: O/W foundation | % wt |
|---|---|---|
| | Phase A | |
| 1 | Stearic Acid | 3.00 |
| 2 | Glyceryl Stearate (and) PEG-100 Stearate | 2.00 |
| 3 | Caprylic/Capric Triglyceride | 3.00 |
| 4 | *Limnanthes Alba* (meadow foam) Seed Oil | 2.40 |
| 5 | Mineral Oil | 1.00 |
| 6 | Ethylhexyl Methoxycinnamate | 3.00 |
| 7 | Dimethicone | 5.00 |
| 8 | Phenyl Trimethicone | 2.00 |
| 9 | Example material 14 | 5.00 |
| | Phase B | |
| 10 | Distilled Water | To 100.00% wt |
| 11 | Sodium Acrylates Copolymer (and) *Glycine Soja* (Soybean Oil) (and) PPG-1 Trideceth-6 | 0.25 |
| 12 | Butylene Glycol | 8.00 |
| 13 | Titanium Dioxide | 9.50 |
| 14 | Iron Oxides Yellow | 1.50 |
| 15 | Iron Oxides Red | 0.35 |
| 16 | Iron Oxide Black | 0.10 |
| 17 | Talc | 1.00 |
| 18 | Triethanolamine | 0.90 |
| 19 | Propylene Glycol (and) Diazolidinyl Urea (and) Methylparaben (and) Propylparaben | q.s. |

Procedure to prepare the O/W foundation of Example 3:

1. Add ingredient 12 to ingredients 13, 14, 15, 16 and 17 to form pigment mix. Mix and then mill three times in 3-roll-mill.
2. Combine phase A ingredients and mix.
3. Heat to 80° C.
4. Heat distilled water to 85° C.
5. Add ingredient 18 to distilled water.
6. Add phase A to distilled water and shear at high speed.
7. Reduce the shear and add pigment mix.
8. Mix for 5 minutes.
9. Add ingredient 11.
10. Add ingredient 10.

Example 4: Bi-Phasic Leave-in Conditioner

| Ingredients of Example 4: bi-phase leave-in conditioner | % wt |
|---|---|
| Phase A | |
| Panthenol | 0.30 |
| Distilled water | To 100.00% wt |
| Glycerin | 1.00 |
| Cetrimonium Chloride | 3.00 |
| Polyquaternium-11 | 0.30 |
| Cocamide MEA | 0.50 |
| Methylchloroisothiazolinone (and) Methylisothiazolinone | 0.10 |
| Phase B | |
| Propylene Glycol | 2.00 |
| Perfume | 0.40 |
| Phase C | |
| Example material 4 | 2.50 |

Procedure to prepare the bi-phase leave-in conditioner of Example 4:
1. Mix ingredients of phase A together until homogeneous.
2. Mix ingredients of phase B together.
3. Add phase B to phase A with mixing.
4. Add phase C to phase AB.
5. Mix until a homogeneous solution is obtained.

Example 5: Liquid Tinted Lip Care

| Ingredients of Example 5: liquid tinted lip care | % wt |
|---|---|
| Phase A | |
| Diisostearyl Malate | 10.0 |
| Squalane | 10.0 |
| Dextrin Palmitate | 3.0 |
| Petrolatum | 10.0 |
| Hydrogenated polyisobutene | 45.0 |
| Phase B | |
| Iron Oxides Red | 0.5 |
| Polyglyceryl-2 Diisostearate | 2.0 |
| Titanium Dioxide (and) Mica (and) Tin Oxide | 3.0 |
| Red 7 Lake | 0.5 |
| Phase C | |
| Silica Silylate | 1.0 |
| Phase D | |
| Diphenylmethylsiloxy Phenyl Methicone/Phenyl Silsesquioxane | 5.0 |
| Phenyl trimethicone | 5.0 |
| Example material 30 | 5.0 |

Procedure to prepare the liquid tinted lip care of Example 5:
1. Mix phase B ingredients together.
2. Mill the phase B mixture to reduce the particle size of the suspended pigment powder. The use of a three-roll mill is recommended.
3. Mix phase A ingredients at 80° C. until completely melted.
4. Mix phase D ingredients at 80° C. until homogeneous
5. Add phase B to phase A and mix until fully homogeneous
6. Add phase C with mixing.
7. Add phase D with mixing.
8. Cool down.

In such tinted or pigmented compositions, the pigments, fillers and emollients may be replaced by any typical of such pigments, fillers and emollients as best suits the formulation requirements for color and/or sensory feel.

Example 6: Hair Serum

| Ingredients of Example 6: hair serum | % wt |
|---|---|
| Phase A | |
| Cyclopentasiloxane | 45.0 |
| Caprylyl Methicone | 20.0 |
| Argan oil | 0.1 |
| Olive Oil | 0.1 |
| Phenyl Trimethicone | 2.0 |
| Cyclopentasiloxane (and) Dimethiconol | 27.7 |
| Example material 1 | 5.0 |
| Perfume (choice) | 0.1 |

Procedure to prepare the hair serum of Example 6: Mix all ingredients until homogeneous.

Example 7: Antiperspirant

| Ingredients of Example 7: antiperspirant | % wt |
|---|---|
| Phase A | |
| Dimethicone (and) Trisiloxane | 65.0 |
| Example material 6 | 5.0 |
| Phase B | |
| Dimethicone (and) Dimethicone Crosspolymer | 15.0 |
| Aluminum Zirconium Tetrachlorohydrex GLY | 15.0 |

Procedure to prepare the antiperspirant of Example 7:
1. Mix phase A until uniform
2. Add phase B into Phase A.
3. Mix with high stirring speed until homogeneous.

Example 8: Rinse Off Conditioner

| Ingredients of Example 8: rinse off conditioner | % wt |
|---|---|
| Phase A | |
| Cetearyl Alcohol | 4.5 |
| Behentrimonium Chloride | 1.5 |
| Example material 7 | 4.0 |
| Phase B | |
| Distilled water | To 100.0 |
| EDTA | 0.1 |
| PEG-32 | 1.0 |
| Polyquaternium-10 | 0.3 |
| Guar Hydroxypropyltrimonium Chloride | 0.2 |
| Phase C | |
| Propylene Glycol | 2.0 |
| Piroctone Olamine | 0.5 |
| Menthol | 0.3 |
| Phase D | |
| Water, *matricaria*, marigold and meadowsweet flowers | 0.3 |
| Propylene Glycol (and) Diazolidinyl Urea (and) Methylparaben (and) Propylparaben | 0.5 |
| Perfume | q.s. |

Procedure to prepare the rinse off conditioner of Example 8
1. Mix phase A ingredients together and heat to 80° C.
2. Mix phase B ingredients together and heat to 80° C.
3. Add phase A to phase B with high shear mixing.
4. Gradually cool to 45° C. while stirring.
5. Mix Phase C ingredients until completely dissolved. Add the mixture of Phase C into Phase AB.
6. Add Phase D ingredients one at a time in the mixture of ABC.
7. Mix until homogeneous.

Diluted samples (6% of example material into 2 cSt polydimethylsiloxane) of Example material 13, Example material 15 and Example material 17 were compared to a commercial material of DOW CORNING® 3901 LIQUID SATIN BLEND, all at 6% active in polydimethylsiloxane of 2 cSt viscosity. Commercially available hair tresses (Virgin Caucasian hair from IHIP, 2 g/25 cm) were washed, dried and then 100 µl of 6% solution in 2 Cst of the materials in Table 12 were applied and spread with a comb on each tress. The tress was then left to dry overnight around a rod spiral curler in the oven at 40 C. The tresses are carefully unrolled then hung in the humidity chamber (70% HR, 25 C). After 5 hours, the tresses are removed from the humidity chamber and have been manually examined to determine the touch and feel.

The diluted sample of Example material 13 had a less slippery feel, nice conditioning, and natural feel as compared to the diluted sample of DOW CORNING® 3901 LIQUID SATIN BLEND. The diluted samples of Example materials 15 and 17 had an intermediate conditioning and feel as compared to the diluted sample of DOW CORNING® 3901 LIQUID SATIN BLEND.

The hair care cosmetic compositions of the invention provide conditioning of the hair while preserving the natural feel of the fibres.

Example 9: Biphasic Leave-In Conditioner

|   | Ingredients of Example 9 | % wt |
|---|---|---|
|   | Phase A |   |
| 1 | Example material 40 | 3 |
| 2 | Dimethicone | 12.4 |
| 3 | Isododecane | 12.4 |
| 4 | Fragrance | 0.2 |
| 5 | Ethylhexyl Methoxycinnamate | 1 |
| 6 | PEG-7 Dimethicone (and) Laureth-7 (and) Polysorbate 20 | 2 |
|   | Phase B |   |
| 7 | Deionized Water | 65.3 |
| 8 | Glycerin | 3 |
| 9 | Laurdimonium Hydroxypropyl Hydrolyzed Keratin | 0.1 |
| 10 | Panthenol | 0.1 |
| 11 | Phenoxyethanol (and) Ethylhexylglycerin | 0.5 |

Procedure to prepare the Biphasic Leave-in Conditioner of Example 9:
1. Mix ingredients 1, 2, and 3 together until homogeneous.
2. Combine remaining Phase A ingredients with the premix made in step 1 and mix until homogeneous.
3. Mix Phase B ingredients together and add to Phase A with mixing.

Example 10: Hair Oil

|   | Ingredient of Example 10 | Wt. % |
|---|---|---|
|   | Phase A |   |
| 1 | Example material 41 | 20 |
| 2 | Dimethicone | 78.3 |
| 3 | Simmondsia Chinensis (Jojoba) Seed Oil | 0.5 |
| 4 | Helianthus Annuus (Sunflower) Oil | 0.5 |
| 5 | Prunus Amygdalus Dulcis (Sweet Almond) Oil | 0.5 |
| 6 | Fragrance | 0.2 |

Procedure to prepare the Hair Oil of Example 10:
1. Mix ingredients 1 and 2 together until homogeneous.
2. Add remaining Phase A ingredients in order while mixing.

Example 11: Conditioning Shampoo

|   | Ingredient of Example 11 | Wt. % |
|---|---|---|
|   | Phase A |   |
| 1 | Deionized Water | 33.1 |
| 2 | Acrylates Copolymer | 6 |
| 3 | Sodium Laureth Sulfate, Aqua | 30 |
|   | Phase B |   |
| 4 | Cocamidopropyl Betaine | 10 |
| 5 | PEG-4 rapeseed amide | 2 |
|   | Phase C |   |
| 6 | Deionized Water | 10 |
| 7 | Polyquaternium-10 | 0.1 |
|   | Phase D |   |
| 8 | Propylene Glycol | 0.25 |
| 9 | Emulsion of example material 42 | 3.3 |
| 10 | Cocamidopropyl Betaine & Glycol Distearate & Laureth-4 | 5 |
| 11 | Panthenol | 0.05 |
| 12 | Phenoxyethanol (and) Ethylhexylglycerin | 0.2 |
| 13 | Sodium Hydroxide | q.s. |

Procedure to prepare the 2-in-1 Conditioning Shampoo of Example 11:
1. Add ingredient 2 in ingredient 1 and mix slowly
2. Add ingredient 3 with gently mixing
3. Adjust pH to 6.5-7 with ingredient 13
4. Add phase B ingredients to phase A with gently mixing
5. In a separate vessel combine phase C ingredients and heat to 40° C. and mix until completely dissolved
6. Add phase C to AB with gently mixing
7. Add phase D ingredients to ABC and mix until uniform
8. Adjust pH with Sodium Hydroxide to 6-6.5 if needed.

Example 12: Roll-on Antiperspirant

|   | Ingredients of Example 12 | % wt |
|---|---|---|
|   | Phase A |   |
| 1 | Example material 42 | 10 |
| 2 | Dimethicone (and) Trisiloxane (and) Disiloxane | 27.5 |
| 3 | Dimethicone (and) Cyclohexasiloxane (and) Cyclopentasiloxane | 27.5 |
|   | Phase B |   |
| 4 | Isododecane (and) Disteardimonium Hectorite (and) Hectorite | 15.0 |
| 5 | Aluminum Sesquichlorohydrate | 20 |

Procedure to prepare the Roll-on antiperspirant of Example 12:
1. Mix phase A until uniform
2. Add phase B into Phase A.
3. Mix with high stirring speed until homogeneous.

Example 13: Oil in Water Sun Screen Cream

| | Ingredients of Example 13 | Wt. % |
|---|---|---|
| | Phase A | |
| 1 | Butyl Methoxydibenzoylmethane | 3 |
| 2 | Octocrylene | 3.6 |
| 3 | Ethylhexyl Methoxycinnamate | 5 |
| 4 | Ethylhexyl Salicylate | 5 |
| | Phase B | |
| 5 | Isohexadecane | 5 |
| 6 | Trimethylsiloxysilicate (and) Polypropylsilsesquioxane | 4 |
| 7 | Caprylyl Methicone | 4.4 |
| 8 | PEG-12 Dimethicone | 4 |
| 9 | Example material 43 | 3 |
| | Phase C | |
| 10 | Decyl Glucoside | 0.5 |
| 11 | Glycerin | 5 |
| 12 | Deionized Water | 55.2 |
| 13 | Polyacrylamide (and) C13-14 Isoparaffin (and) Laureth-7 | 2 |
| 14 | DMDM Hydantoin | 0.3 |

Procedure to prepare the Oil in Water sun screen cream of Example 13:
1. Mix phase A ingredients together and heat to 80-85° C. until homogeneous.
2. Cool down to room temperature while continue mixing.
3. Mix Phase B ingredients until homogeneous.
4. Add phase A to phase B mixing until homogeneous.
5. Mix phase C ingredients together.
6. Add mixture of phase A and B to phase C under agitation.
7. Add phase D to mixture ABC. Mix until homogeneous.

In such sunscreen compositions, the sun filters and emollients may be replaced by any typical of such sunfilters and emollients as best suits the formulation requirements for sun protection and/or sensory feel.

Example 14: Foaming Cleanser

| | Ingredients of Example 14 | % wt |
|---|---|---|
| | Phase A | |
| 1 | Distilled Water | To 100% wt |
| 2 | *Actinidia Chinensis* (Kiwi) Fruit Water | 20.0 |
| 3 | Sodium Laureth Sulfate | 6.0 |
| 4 | Decyl Glucoside | 5.0 |
| 5 | Cocamidopropyl Hydroxysultaine | 3.0 |
| | Phase B | |
| 6 | Acrylates Copolymer | 8.0 |
| | Phase C | |
| 7 | *Simmondsia Chinensis* (Jojoba) Seed Oil | 1.0 |
| 8 | Propylene Glycol (and) Diazolidinyl Urea (and) Methylparaben (and) Propylparaben | q.s. |
| 9 | Emulsion of example material 41 or 42 | 8.0 |
| | Phase D | |
| 10 | Sodium Hydroxide (10% wt solution in water) | 1.7 |

Procedure to prepare the foaming cleanser of Example 14:
1. Add Ingredients of Phase A one by one in order of addition with gently mix, wait after each addition until homogeneous.
2. Add Phase B ingredient to Phase A with gentle mix.
3. Adjust pH to 6.5-7 with ingredient 10
4. Add Phase C ingredients to Phase AB with mixing.
5. Adjust pH to 6-6.5 with ingredient 10.

Example 15: O/W Liquid Foundation

| | Ingredients of Example 15: O/W foundation | % wt |
|---|---|---|
| | Phase A | |
| 1 | PEG-12 Dimethicone | 2 |
| 2 | Ethylhexyl Salicylate | 2 |
| 3 | Ethylhexyl Methoxycinnamate | 5 |
| 4 | Trilaureth-4 Phosphate | 0.30 |
| 5 | Bisabolol (and) *Zingiber Officinale* (Ginger) Root | 0.1 |
| 6 | Dimethicone | 12 |
| 7 | Pentaerythrityl tetraethylhexanoate | 2 |
| | Phase B | |
| 8 | Distilled Water | 48.84 |
| 9 | Glycerin | 3 |
| 10 | Acrylates Copolymer | 2 |
| | Phase C | |
| 11 | CI 77891 (and) Aqua (and) Glycerin (and) Xanthan gum | 16 |
| 12 | CI 77499 (and) Aqua (and) Glycerin (and) Xanthan gum | 0.16 |
| 13 | CI 77492 (and) Aqua (and) Glycerin (and) Xanthan gum | 2 |
| 14 | CI 77491 (and) Aqua (and) Glycerin (and) Xanthan gum | 0.4 |
| | Phase D | |
| 15 | Example material 42 | 3.5 |
| | Phase E | |
| 16 | Sodium Hydroxide (18%) | 0.4 |
| | Phase F | |
| 17 | Phenoxyethanol (and) Ethylhexylglycerin | 0.3 |

Procedure to prepare the O/W liquid foundation of Example 15:
1. Mix phase A ingredients until homogeneous.
2. Mix phase B ingredients until homogeneous.
3. Add phase C to phase B and mix.
4. Add phase A to phase BC and mix.
5. Add phase D to phase ABC and mix until uniform.
6. Adjust pH to 6.5 with Sodium Hydroxide solution.
7. Add phase F with mixing.
8. Add ingredient 10.

Curl Retention Test:

The Curl Retention test is designed to evaluate ability of products or formulations to maintain the curly shape of the hair under defined humidity conditions.

Commercially available hair tresses (Virgin Caucasian hair from IHIP, 2 g/25 cm) were washed, dried and then 100 µl of 6% solution in 2 Cst of the materials in Table 12 were applied and spread with a comb on each tress. The tress was then left to dry overnight around a rod spiral curler in the oven at 40 C.

The tresses are carefully unrolled then hung in the humidity chamber (70% HR, 25 C). Hair tress length is measured at determined intervals of time: T=0, 10, 20, 30, 40, 50, 60, 90, 120, 180, 240, 300 minutes. After 5 hours, the tresses are removed from the humidity chamber and the tress length is measured at its maximum, by unrolling it completely.

Percent curl retention is calculated as follows:

$$\% \text{ Curl Retention} = (\text{max length} - \text{length at } T=x)/(\text{max length} - \text{length at } T=0) \times 100$$

At least 3 tresses per sample are used. The data in the table is an average of the values obtained for the 3 tresses for each time interval.

TABLE 12

| Time (min) | Dow Corning ® 3901 Liquid Satin Blend (INCI: Dimethicone (and) Dimethicone/Vinyl Dimethicone Crosspolymer) | Example Material 40 | Example Material 41 | Example Material 42 | Dow Corning ® 200 Fluid, 2 cSt (INCI: Dimethicone) |
|---|---|---|---|---|---|
| 0 | 100 | 100 | 100 | 100 | 100 |
| 10 | 75.18 | 78.28 | 73.51 | 73.56 | 64.86 |
| 20 | 66.79 | 69.32 | 62.76 | 61.95 | 50.73 |
| 30 | 62.11 | 62.88 | 55.52 | 53.84 | 41.69 |
| 40 | 59.05 | 60.06 | 52.00 | 50.53 | 37.39 |
| 50 | 56.11 | 57.36 | 49.87 | 47.65 | 34.38 |
| 60 | 53.45 | 54.97 | 46.80 | 44.44 | 32.30 |
| 90 | 51.98 | 52.67 | 44.13 | 42.32 | 30.79 |
| 120 | 50.38 | 50.18 | 42.11 | 39.44 | 29.05 |
| 180 | 48.77 | 49.14 | 40.62 | 37.73 | 26.15 |
| 240 | 47.80 | 48.62 | 39.66 | 36.88 | 25.57 |
| 300 | 47.36 | 47.79 | 39.34 | 36.45 | 25.11 |

Example materials 40, 41 and 42 are providing better curl retention than dimethicone. Example material 40 is giving stronger hold among the 3 samples, equivalent to the performance of the comparative benchmark Dow Corning® 3901 Liquid Satin Blend.

Hair treated with example materials felt smooth and slippery with a pleasant and natural feel. The advantage of the Example materials in addition to performance, is the ease of handling and diluting, as compared to some other benchmarks with particular rheology profiles.

The invention claimed is:

1. A cosmetic composition comprising:
   a silicone based material cured via a condensation cure chemistry; and
   at least one cosmetic ingredient,
   optionally in a cosmetically acceptable medium;
   wherein the silicone based material is a condensation reaction product of a reaction of:
   (i) at least one condensation curable silyl terminated polymer having at least one, optionally at least two hydrolysable and/or hydroxyl functional groups per molecule;
   (ii) a cross-linker selected from the group consisting of monosilane cross-linkers having at least two hydrolysable groups and/or disilyl cross-linkers having at least two silyl groups, where each silyl group contains at least one hydrolysable group; and
   (iii) a condensation catalyst having M-OR functions and selected from the group consisting of titanates and/or zirconates;
   wherein the molar ratio of hydrolysable and/or hydroxyl functional group(s) of the at least one condensation curable silyl terminated polymer to hydrolysable groups of the cross-linker is between 0.4:1 to 2:1 using a monosilane cross-linker or is between 0.2:1 to 10:1 using a disilyl cross-linker; and
   wherein the molar ratio of condensation catalyst M-OR functions to the hydrolysable and/or hydroxyl group(s) of the at least one condensation curable silyl terminated polymer is between 0.01:1 and 0.6:1, where M is titanium or zirconium and R is an aliphatic hydrocarbon.

2. The cosmetic composition of claim 1, wherein the at least one cosmetic ingredient is different from a filler.

3. The cosmetic composition of claim 1, wherein the silicone based material is in neat form, in diluted form, or in emulsion form.

4. The cosmetic composition of claim 1, wherein the at least one cosmetic ingredient is selected from the group consisting of emollients, waxes, moisturizers, surface active materials, thickeners, water phase stabilizing agents, pH controlling agents, preservatives and cosmetic biocides, sebum absorbants, sebum control agents, vegetable extracts, botanical extracts, vitamins, proteins and their derivatives, amino-acids and their derivatives, pigments, colorants, fillers, silicone conditioning agents, cationic conditioning agents, UV absorbers, sunscreen agents, antidandruff agents, antiperspirant agents, deodorant agents, skin protectants, hair dyes, nail care ingredients, fragrances, perfume, antioxidants, oxidizing agents, reducing agents, film formers, propellant gases, fatty alcohols, color care additives, pearlising agents, chelating agents, film formers, styling agents, ceramides, suspending agents, and mixtures thereof.

5. The cosmetic composition of claim 1, wherein the at least one cosmetic ingredient is selected from the group consisting of surface active materials, preservatives and cosmetic biocides.

6. The cosmetic composition of claim 1, which is in the form of a cream, a gel, a free flowing powder, a pressed powder, a paste, a solid, a freely pourable liquid, or an aerosol.

7. The cosmetic composition of claim 1, which is in the form of a shampoo, a cream, a rinse-off conditioner, a leave-in conditioner, or a gel.

8. A process for preparing the cosmetic composition of claim 1, the process comprising:
   mixing the silicone based material; and
   the at least one cosmetic ingredient, optionally in the presence of a cosmetically acceptable medium.

9. The process according to claim 8, wherein the cosmetic composition is prepared by mixing the silicone based material in neat form with the ingredients of a hydrophobic phase, optionally under heating.

10. The process according to claim 8, wherein the cosmetic composition is prepared by mixing the silicone based material in emulsion form with the ingredients of a hydrophilic phase, optionally under heating.

11. The process according to claim 10, wherein the emulsion form of the silicone based material is made with partially cured silicone based material cured via a condensation cure chemistry, followed by the post-cure of already emulsified silicone based material cured via a condensation cure chemistry.

12. A process to care for keratinous substrates comprising the steps of:
- providing a cosmetic composition comprising a silicone based material cured via a condensation cure chemistry, and at least one cosmetic ingredient, optionally in a cosmetically acceptable medium; and
- applying the cosmetic composition to the keratinous substrate;
- and optionally rinsing;
- wherein the silicone based material is a condensation reaction product of a reaction of:
  - (i) at least one condensation curable silyl terminated polymer having at least one, optionally at least two hydrolysable and/or hydroxyl functional groups per molecule;
  - (ii) a cross-linker selected from the group consisting of monosilane cross-linkers having at least two hydrolysable groups and/or disilyl cross-linkers having at least two silyl groups, where each silyl group contains at least one hydrolysable group; and
  - (iii) a condensation catalyst having M-OR functions and selected from the group consisting of titanates and/or zirconates;
  - wherein the molar ratio of hydrolysable and/or hydroxyl functional group(s) of the at least one condensation curable silyl terminated polymer to hydrolysable groups of the cross-linker is between 0.4:1 to 2:1 using a monosilane cross-linker or is between 0.2:1 to 10:1 using a disilyl cross-linker; and
  - wherein the molar ratio of condensation catalyst M-OR functions to the hydrolysable and/or hydroxyl group (s) of the at least one condensation curable silyl terminated polymer is between 0.01:1 and 0.6:1, where M is titanium or zirconium and R is an aliphatic hydrocarbon.

13. The cosmetic composition of claim 1, wherein the at least one condensation curable silyl terminated polymer has at least two hydrolysable and/or hydroxyl functional groups per molecule.

14. The process according to claim 12, where the at least one condensation curable silyl terminated polymer has at least two hydrolysable and/or hydroxyl functional groups per molecule.

* * * * *